(12) United States Patent
Torii et al.

(10) Patent No.: US 10,577,135 B2
(45) Date of Patent: Mar. 3, 2020

(54) METHOD FOR FILLING PARTICULATE WATER ABSORBING AGENT AND METHOD FOR SAMPLING FILLED PARTICULATE WATER ABSORBING AGENT

(71) Applicant: NIPPON SHOKUBAI CO., LTD., Osaka-shi, Osaka (JP)

(72) Inventors: Kazushi Torii, Himeji (JP); Shigeru Sakamoto, Himeji (JP); Kenji Tada, Himeji (JP); Kazuki Kimura, Himeji (JP); Yusuke Watanabe, Himeji (JP)

(73) Assignee: NIPPON SHOKUBAI CO., LTD., Osaka-shi, Osaka (JP)

( * ) Notice: Subject to any disclaimer, the term of this patent is extended or adjusted under 35 U.S.C. 154(b) by 511 days.

(21) Appl. No.: 15/024,733

(22) PCT Filed: Sep. 30, 2014

(86) PCT No.: PCT/JP2014/076200
§ 371 (c)(1),
(2) Date: Mar. 24, 2016

(87) PCT Pub. No.: WO2015/046604
PCT Pub. Date: Apr. 2, 2015

(65) Prior Publication Data
US 2016/0236803 A1 Aug. 18, 2016

(30) Foreign Application Priority Data

Sep. 30, 2013 (JP) .................................. 2013-203059
Apr. 23, 2014 (JP) .................................. 2014-089598

(51) Int. Cl.
*B65B 1/22* (2006.01)
*B01J 20/26* (2006.01)
(Continued)

(52) U.S. Cl.
CPC ............... *B65B 1/22* (2013.01); *B01J 20/267* (2013.01); *B01J 20/28011* (2013.01);
(Continued)

(58) Field of Classification Search
CPC ..... B65B 1/22; B01J 20/267; B01J 20/28011; B01J 20/28016
See application file for complete search history.

(56) References Cited

U.S. PATENT DOCUMENTS 6,716,894 B2 4/2004 Kajikawa et al.
6,727,345 B2 4/2004 Kajikawa et al.
(Continued)

FOREIGN PATENT DOCUMENTS

CN 101970299 A 2/2011
JP A-2003-82107 4/1991
(Continued)

OTHER PUBLICATIONS

International Search Report dated Dec. 22, 2014 in PCT Application No. PCT/JP2014/076200.
(Continued)

*Primary Examiner* — Christine A Enad
(74) *Attorney, Agent, or Firm* — Dickinson Wright PLLC

(57) ABSTRACT

An object of the invention is to provide a technique in which a decrease in physical properties is suppressed or consumer complaints are diminished. A method includes a filling step of filling a particulate water absorbing agent into a filling container and a vibrating step of vibrating the filling container at the outside of the filling container, the vibrating step being conducted at least one time between the start and the end of the filling step. A vibration condition in the vibrating step satisfies the following conditions: (a) vibration by a vibrating body in contact with the filling container has a vertical directional component and a vibrational angle is (Continued)

within 90°±30°; and (b) total amplitude at no load and a vibration frequency at no load of the vibrating body are set so as to satisfy Equation 1-1 and Equation 2 or Equation 1-2 and Equation 2.

8 Claims, 1 Drawing Sheet

(51) Int. Cl.
  *B01J 20/28* (2006.01)
  *G01N 1/04* (2006.01)
  *B65B 1/06* (2006.01)
(52) U.S. Cl.
  CPC .......... *B01J 20/28016* (2013.01); *G01N 1/04* (2013.01); *B01J 2220/68* (2013.01); *B65B 1/06* (2013.01)

(56) References Cited

U.S. PATENT DOCUMENTS

| | | | |
|---|---|---|---|
| 6,817,557 B2 | 11/2004 | Kakita et al. | |
| 7,193,006 B2 | 3/2007 | Ishizaki et al. | |
| 2003/0020199 A1 | 1/2003 | Kajikawa et al. | |
| 2004/0106745 A1* | 6/2004 | Nakashima | A61L 15/60 525/418 |
| 2005/0155665 A1 | 7/2005 | Schlacchter | |
| 2007/0225160 A1* | 9/2007 | Kitano | C08J 3/203 502/402 |
| 2008/0227932 A1 | 9/2008 | Funk et al. | |
| 2009/0321682 A1 | 12/2009 | Kajikawa et al. | |
| 2011/0003926 A1 | 1/2011 | Nogi et al. | |
| 2011/0009590 A1 | 1/2011 | Matsumoto et al. | |
| 2011/0011491 A1* | 1/2011 | Matsumoto | B65B 1/08 141/72 |
| 2011/0166300 A1 | 7/2011 | Dairoku et al. | |
| 2011/0313113 A1 | 12/2011 | Sakamoto et al. | |
| 2012/0016084 A1* | 1/2012 | Dairoku | C08J 3/12 525/115 |
| 2012/0258851 A1 | 10/2012 | Nakatsuru et al. | |
| 2013/0101851 A1 | 4/2013 | Takaai et al. | |
| 2014/0312273 A1 | 10/2014 | Wattebled et al. | |
| 2015/0367018 A1* | 12/2015 | Oshima | A61L 15/26 604/372 |

FOREIGN PATENT DOCUMENTS

| | | |
|---|---|---|
| JP | A-Ho3-097803 | 3/2003 |
| JP | 2003105092 A | 4/2003 |
| WO | WO 2007/023097 A1 | 3/2007 |
| WO | WO 2008/015946 A1 | 2/2008 |
| WO | WO 2009/113671 A1 | 9/2009 |
| WO | WO 2010/095427 A1 | 8/2010 |
| WO | WO 2011/078298 A1 | 6/2011 |
| WO | WO 2012/002455 A1 | 1/2012 |
| WO | WO 2013/007819 A1 | 1/2013 |
| WO | WO 2013/072268 A1 | 5/2013 |
| WO | WO 2013/120722 A1 | 8/2013 |

OTHER PUBLICATIONS

PCT Notification Concerning Transmittal of International Preliminary Report on Patentability (Chapter 1 of the Patent Cooperation Treaty), dated Apr. 14, 2016 that issued in PCT App. No. PCT/JP2014/076200.
PCT Notification of Transmittal of Translation of the International Preliminary Report on Patentability (Chapter 1 or Chapter II), dated Apr. 14, 2016 that issued in PCT App. No. PCT/JP2014/076200.
Chinese Office Action dated Nov. 7, 2016 which issued in the corresponding Patent Application No. 201480054206.0, including English translation.
European Search Report dated Aug. 17, 2017 which issued in the corresponding European Patent Application No. 14847701.1.
Chinese Office Action, dated Aug. 17, 2017 which issued in the corresponding Application No. 201480054206.0.
Japanese Office Action in related Japanese Application No. 2015-539476, dated Nov. 14, 2017 (with English translation).
Supplementary Partial European Search Report dated May 17, 2017 which issued in the corresponding European Patent Application No. 14847701.1.
Official Notice of Reasons for Refusal dated May 9, 2017 which issued in the corresponding Japanese Patent Application No. 2015-539476, including English translation.
Japanese Office Action dated Nov. 27, 2018, which issued in the corresponding Japanese Patent Application No. 2017-248350, including English translation.
European Office Action dated Feb. 26, 2019, which issued in the corresponding European Patent Application No. 14 847 701.1.
Japanese Notice of Reasons for Refusal dated Sep. 3, 2019, which issued in the counterpart Patent Application No. 2017-248350, including English translation.

* cited by examiner

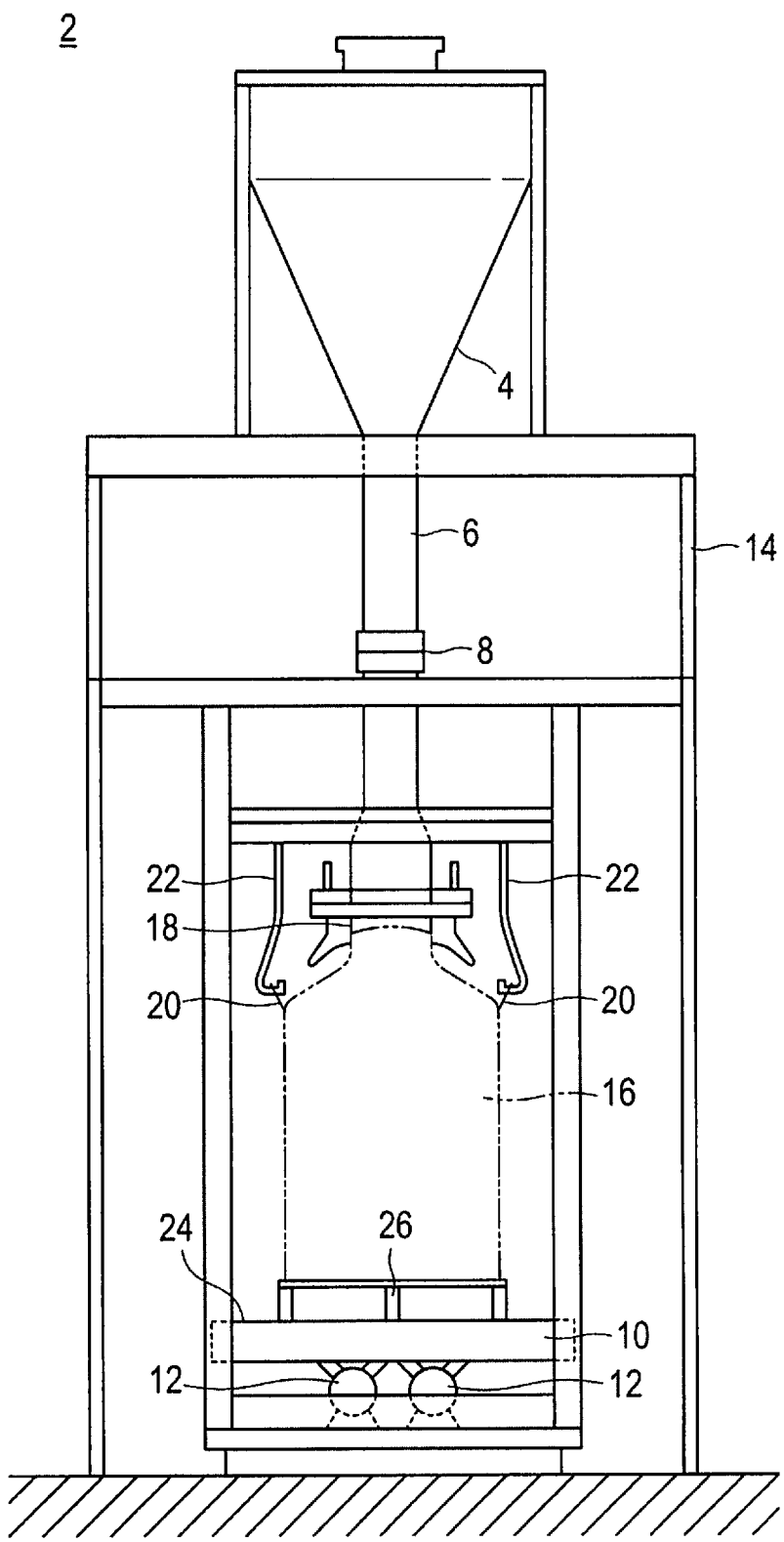

METHOD FOR FILLING PARTICULATE WATER ABSORBING AGENT AND METHOD FOR SAMPLING FILLED PARTICULATE WATER ABSORBING AGENT

TECHNICAL FIELD

The present invention relates to a method for filling a particulate water absorbing agent and a method for sampling a filled particulate water absorbing agent.

BACKGROUND ART

In recent years, water absorbent resins are widely utilized as a water absorbing agent in the sanitary materials such as paper diapers, sanitary napkins, and napkins for incontinents which is a constituent material thereof from the viewpoint of absorption of the body fluids. As such water absorbent resins, for example, a crosslinked product of partially neutralized polyacrylic acid, a hydrolysate of starch-acrylic acid graft polymer, a saponified product of vinyl acetate-acrylic acid ester copolymer, a hydrolysate or a crosslinked product of an acrylonitrile copolymer or an acrylamide copolymer, and a crosslinked product of a cationic monomer are known.

This water absorbent resin is generally used in the water absorbing agent as a powder (particles) although it can be used as a sheet, a fiber, and a film. As the powder (particles), for example, a particulate water absorbing agent having a mass average particle size of about from 200 to 800 μm is widely used. The particulate water absorbing agent is produced through many steps (preferably a continuous process) (for example, Patent Literature 1). In addition, the particulate water absorbing agent is filled in a filling container in the case of shipping this particulate water absorbing agent. The particulate water absorbing agent to be filled is transported by various means of transport to be delivered to the destination (user and the like). As this filling container, for example, a flexible container bag, a portable silo, and the like are used. This flexible container bag is also referred to as a fleconbag for short. Filling is usually conducted using a hopper as described in Patent Literature 2 or the like.

Meanwhile, a particulate water absorbing agent is produced by controlling a number of physical properties (for example, water absorption capacity, water absorption capacity under load, water absorbent speed, liquid permeability, and gel stability) of the parameters as the specifications depending on the intended use (for example, paper diapers and sanitary napkins). Various solving means as to be described below have been proposed in order to solve the problem of stabilization of such physical properties.

For example, Patent Literature 3 discloses a technique to remove the water absorbent resin having the respective physical properties which deviate from the predetermined upper and lower limits and to remix it. Patent Literature 4 discloses a technique to use plural hoppers in an intermediate step. Patent Literature 5 discloses a technique to conduct the polymerization in two systems and then to conduct a mixing treatment. As described above, a number of techniques for improving and stabilizing the physical properties of the particulate water absorbing agent by changing or imparting a new intermediate producing step have been proposed.

Furthermore, in recent years, a particulate water absorbing agent having a high water absorbent speed is desired, and in particular it is aimed to achieve both liquid permeability and water absorbent speed which are the physical properties conflicting with each other (Patent Literatures 6 to 12).

Meanwhile, there is not only a technique to precisely control the physical properties of the particulate water absorbing agent as described above but also a technique to eliminate a factor that causes a decrease in physical properties of the final product (for example, paper diapers) or consumer complaints by focusing on the fact that the deflection of the running conditions in the filling step to fill the produced particulate water absorbing agent causes a great deflection of the physical properties of the final product (for example, paper diapers) (Patent Literature 13).

CITATION LIST

Patent Literatures

Patent Literature 1: U.S. Pat. No. 6,716,894
Patent Literature 2: U.S. Pat. No. 6,817,557
Patent Literature 3: U.S. Pat. No. 7,193,006
Patent Literature 4: U.S. Pat. No. 6,727,345
Patent Literature 5: WO 2007/023097
Patent Literature 6: WO 2008/015946
Patent Literature 7: WO 2013/120722
Patent Literature 8: WO 2013/072268
Patent Literature 9: WO 2013/007819
Patent Literature 10: WO 2012/002455
Patent Literature 11: WO 2011/078298
Patent Literature 12: WO 2010/095427
Patent Literature 13: WO 2009/113671

SUMMARY OF INVENTION

Technical Problem

Usually, the produced particulate water absorbing agent is (I) filled in a filling container by from several hundreds of kg to several thousands of kg as one unit, (II) transported to a location for manufacturing an absorbent article (for example, paper diapers), and (III) completed as a final product (absorbent article) by being contained at from 0.1 g to 100 g as one unit.

According to the technique of Patent Literature 13, it is attempted to eliminate a factor that causes a decrease in physical properties of the final product (for example, paper diapers) or consumer complaints by providing a method for filling a particulate water absorbing agent which can fill the particulate water absorbing agent in a less segregated state at the stage of (I) above, and an improvement is achieved to a certain extent. However, the present inventors have found that there is room for further improvement.

In addition, on the other hand, it is required to show the specifications (namely, the representative values of the respective water absorption physical properties) of the filled particulate water absorbing agent filled in the respective filling containers to clients at the stage of (I) above. In addition, there is a requirement to confirm the specifications of the filled particulate water absorbing agent again depending on the intended use (for example, for paper diapers and sanitary napkins) and the like at the stage of (III) above as well in some cases, and thus, high precision is required for the sampling in order to know the respective specifications. It is possible to suppress a decrease in physical properties depending on the lot and to diminish the consumer complaints if it is possible to provide a highly precise sampling technique.

Hence, an object of the invention is to provide a method for filling a particulate water absorbing agent which can significantly decrease the variation of water absorption physical property values of the respective final products (absorbent articles) and a method for determining the specifications of the filled particulate water absorbing agent by providing a highly precise sampling method of a filled particulate water absorbing agent, thereby providing a technique in which a decrease in physical properties is suppressed or consumer complaints are diminished.

Solution to Problem

The present inventors have conducted intensive studies to solve the above problems. In the course, first, the present inventors have focused on the stage of (II) above. In other words, in the stage of (I) above, the particulate water absorbing agent is filled in a filling container by from several hundreds of kg to several thousands of kg as one unit and thus the filling container is usually transported by a means of transport such as a truck. The present inventors have focused on the "jolting" during this transport. In other words, it has been found out that segregation can be caused by the "jolting" during transport even in a case in which a less segregated state is achieved at the stage of (I) above. In the invention, it has been found out that it is possible to provide a filled particulate water absorbing agent exhibiting significantly less segregation not only at the stage of (I) above but also at the stage of (III) above by densely packing the filled particulate water absorbing agent by a filling method in which the "acceleration [G]" and the "vibration index" are in a specific relation in the filling method carried out while applying vibration to the particulate water absorbing agent via the container at the stage of (I) above in anticipation of the "jolting" during transport, and thus it is possible to significantly decrease the variation of water absorption physical property values of the respective final products (absorbent articles).

In addition, it has been found out that, by providing a method for sampling a filled particulate water absorbing agent having a filling volume of V (cm³), in which a sampling number n (times) and a distance x (cm) among the respective sampling points adjacent to one another are set such that the following conditions (1) and (2) are necessarily satisfied:

[Mathematical Formula 1]

$$n \geq m \quad (1)$$

with the proviso that, m is greater one of 3 and $$\lfloor V/100000 \rfloor \quad \text{[Mathematical Formula 2]}$$

[Mathematical Formula 3]

$$x \geq y \quad (2)$$

with the proviso that, $$y = \frac{\sqrt[3]{V}}{\left[\sqrt[3]{m}\right]+1} \quad \text{[Mathematical Formula 4]}$$

it is possible to sample a filled particulate water absorbing agent with high precision and to determine the specifications thereof with high precision.

Advantageous Effect of the Invention

According to the invention, it is possible to significantly decrease the variation of water absorption physical property values of the respective final products (absorbent articles) and to provide a highly precise sampling method of a filled particulate water absorbing agent, and thus it is possible to provide a technique in which a decrease in physical properties is suppressed or consumer complaints are diminished.

BRIEF DESCRIPTION OF DRAWINGS

FIG. 1 is a view illustrating an example of a filling apparatus 2 usable in the invention.

DESCRIPTION OF EMBODIMENTS

Hereinafter, an embodiment of the invention will be described in detail, but the scope of the invention is not confined to these descriptions. Embodiments other than the following illustrative embodiment may be appropriately performed within the scope and gist of the invention.

DEFINITION OF TERMS

First, the definitions of representative terms described in the present specification will be described.

(a) "Water Absorbent Resin"

In the present specification, the term "water absorbent resin" means a polymer gelling agent that is swellable in water and insoluble in water, and it refers to those having the following physical properties. In other words, the water absorbent resin refers to a polymer gelling agent of which the centrifuge retention capacity (CRC/defined in Example) is essentially 5 (g/g) or more, preferably from 10 (g/g) to 100 (g/g) and more preferably from 20 (g/g) to 80 (g/g) and the water-soluble content (Extractables/defined in ERT450.2-02 (2002)) is preferably from 0% by weight to 50% by weight, more preferably from 0% by weight to 30% by weight, still more preferably from 0% by weight to 20% by weight, and particularly preferably from 0% by weight to 10% by weight. Incidentally, the water absorbent resin is not limited to an embodiment in which the entire amount (100%) thereof is composed of a polymer, but it may contain an additive to be described later and the like in a range in which the performance described above is maintained.

However, in the following description, there is a case in which the water absorbent resin is described as a particulate water absorbing agent for convenience.

(b) "Polyacrylic Acid (Salt)"

In the present specification, the term "polyacrylic acid (salt)" means a polymer which contains acrylic acid (salt) as the main component of the repeating unit. Specifically, it means a polymer which contains acrylic acid (salt) at preferably from 50% by mole to 100% by mole, more preferably from 70% by mole to 100% by mole, still more preferably from 90% by mole to 100% by mole, and particularly preferably substantially 100% by mole as the monomer excluding the crosslinking agent. The salt as a polymer preferably contains a water-soluble salt, more preferably a monovalent salt, and still more preferably an alkali metal salt or an ammonium salt. Among them, in practice, an alkali metal salt is particularly preferable and a sodium salt is further preferable.

(c) "Water Absorbing Agent"

In the present specification, the term "water absorbing agent" means a gelling agent which contains a water absorbent resin as the main component and absorbesan aqueous liquid. Incidentally, the aqueous liquid is not limited to water, but it may be urine, blood, feces, waste liquid, moisture or vapor, ice, a mixture of water and an organic solvent and/or an inorganic solvent, rain water, ground water, and the like, and the aqueous liquid is not particularly limited as long as it contains water. Among them, examples of the aqueous liquid may include more preferably urine and particularly preferably human urine. The content of the water absorbent resin (a polyacrylic acid (salt)-based water absorbent resin) in the invention is preferably from 70% by weight to 99.9% by weight, more preferably from 80% by weight to 99.7% by weight, and still more preferably from 90% by weight to 99.5% by weight based on the entire water absorbing agent. As other components other than the water absorbent resin, water is preferable from the viewpoint of water absorbent speed or impact resistance of the powder (particles), and the additives to be described later are contained if necessary.

(d) "EDANA" and "ERT"

The "EDANA" is the abbreviation of the European Disposables and Nonwovens Association, and the "ERT" is the abbreviation of the measuring method of water absorbent resin (ERT/EDANA Recommended Test Methods) of the European standard (substantially world standard). In the present specification, the physical properties of the water absorbent resin are measured with reference to the original ERT (known document: revised in 2002) unless otherwise stated.

(e) "Particle"

In the present specification, the term "particle" means a solid which has a particle size defined by sieve classification of 5 mm or less and exhibits fluidity. The moisture content (defined in ERT 430.2-02) is not particularly limited as long as it is a solid, but the moisture content of the particle is usually less than 30% by weight and more preferably 20% by weight or less. In addition, the lower limit of the particle size is, for example, 1 nm. Moreover, it is sufficient that the particle exhibits fluidity to a certain extent as a powder, and for example, the particle means a solid of which the flow rate (ERT 450.2-02) can be measured or a solid which can be subjected to the sieve classification by (ERT 420.2-02). The shape of the solid is not particularly limited, and examples thereof may include irregular crushed particles, spherical particles, substantially spherical particles, or granules (aggregates) thereof but preferably include irregular crushed particles. In the invention, a particle-like water absorbing agent, namely, a "particulate water absorbing agent" is used.

(f) "CRC" (ERT 441.2-02)

The "CRC" is the abbreviation of the centrifuge retention capacity and means the water absorption capacity of the water absorbent resin without load (hereinafter, also referred to as the "water absorption capacity". In addition, it is synonymous with the "absorption capacity".). Specifically, the CRC is a water absorption capacity (unit; (g/g)) after 0.200 g of the water absorbent resin in a nonwoven bag is immersed (free swelling) in large excess of an aqueous solution of sodium chloride at 0.9% by weight for 30 minutes and then dewatered by a centrifuge.

(g) "AAP" (ERT 442.2-02)

The "AAP" is the abbreviation of the absorbency against pressure and means the water absorption capacity of the water absorbent resin under load. Specifically, the AAP is a water absorption capacity (unit; (g/g)) after 0.900 g of a water absorbent resin is allowed to swell in large excess of an aqueous solution of sodium chloride at 0.9% by weight for 1 hour at a load of 2.06 kPa (0.3 psi, 21 (g/cm$^2$)).

Incidentally, the Absorption Under Pressure is written in ERT442.2-02, but the absorption under pressure is substantially the same as the AAP. In addition, the AAP is measured by changing the load condition to 4.83 kPa (0.7 psi, 50 (g/cm$^2$)) in some cases. In Examples of the invention, it is measured by changing the load condition to 4.93 kPa (0.7 psi, 50 (g/cm$^2$)).

Incidentally, the absorbency against pressure measured at 2.06 kPa is denoted as the "AAP 0.3" and the absorbency against pressure measured at 4.83 kPa is denoted as the "AAP 0.7".

(h) "Ext" (ERT 470.2-02)

The "Ext" is the abbreviation of the extractables and means the water-soluble content (amount of water-soluble component) of the water absorbent resin. Specifically, the Ext is the dissolved amount (unit; % by weight) of polymer after 1.000 g of a water absorbent resin is added to 200 ml of an aqueous solution of sodium chloride at 0.9% by weight and stirred for 16 hours at 500 rpm. The measurement of the dissolved amount of polymer is conducted by pH titration.

(i) "PSD" (ERT 420.2-02)

The "PSD" is the abbreviation of the particle size distribution and means the particle size distribution of a water absorbent resin measured by sieve classification. In addition, the mass average particle size (D50) of the water absorbent resin and the logarithmic standard deviation (σξ) of the particle size distribution are measured by the same methods as the "(3) Mass-Average Particle Diameter (D50) and Logarithmic Standard Deviation (σξ) of Particle Diameter Distribution" described in U.S. Pat. No. 7,638,570.

(j) PSR

The water absorbent speed "FSR" is the abbreviation of the free swell rate and means the water absorbent speed (free swell rate). Specifically, the "FSR" refers to a speed (unit; (g/g/s)) when 1 g of a water absorbent resin absorbs 20 g of an aqueous solution of sodium chloride at 0.9% by weight. The specific measuring method is described in WO 2012/002455 A (paragraphs "0248" to "0253").

(k) Saline Flow Conductivity (SPC)

The saline flow conductivity is the liquid permeability of a water absorbent resin at a load. The specific measuring method is described in Patent Literature 13 (paragraphs "0139" to "0141").

(1) Others

In addition, in the present specification, the expression "from X to Y" which represents a range means that it is "X or more and Y or less". In addition, the "tons (t)" of a unit of weight represents the "metric tons". In addition, in the present specification, the "mass" and the "weight", the "% by mass" and the "% by weight", and the "parts by mass" and the "parts by weight" are synonymous with each other, respectively, and the measurement of physical properties and the like are conducted at room temperature (20° C. to 25° C.) and a relative humidity of from 40% to 50% unless otherwise stated.

<Embodiment of Method for Producing Particulate Water Absorbing Agent>

In the invention, the target material to be filled is a particulate water absorbing agent.

In the present specification, the "particulate water absorbing agent" contains a water absorbent resin as the main component. This "main component" means that the proportion of the water absorbent resin contained is 70% by weight or more based on the particulate water absorbing agent. In other words, the particulate water absorbing agent used in the invention contains a water absorbent resin at 70% by weight or more, preferably from 70% by weight to 99.9% by weight, more preferably from 80% by weight to 99.7% by weight, and still more preferably from 90% by weight to 99.5% by weight. Incidentally, the water absorbent resin is not particularly limited, but a polyacrylic acid (salt)-based water absorbent resin is preferably contained as the main component from the viewpoint of the physical properties.

As the method for producing a water absorbent resin, a known method can be applied, and the particulate water absorbing agent thus produced is then subjected to the filling step. In the filling step, the particulate water absorbing agent is filled in a filling container.

Hereinafter, first, the method for producing a particulate water absorbing agent that can be used in the invention will be described.

According to a preferred embodiment, the method for producing a particulate water absorbing agent can include a polymerizing step, a drying step, a pulverizing step, a classifying step, a surface crosslinking step, a cooling step, a step of adding additives, a sizing step, a granulating step, etc. More specifically, the particulate water absorbing agent can be produced with reference to Patent Literatures 1 to 5 and 13 or by combining them, in particular it is preferably produced in conformity with Patent Literature 13, but the method for producing a particulate water absorbing agent is not particularly limited. Among them, the invention is suitably applied to the filling and transport of a water absorbing agent of a water absorbent resin which has a high water absorbent speed (preferably 0.25 (g/g/s) or more and more preferably from 0.30 (g/g/s) to 0.45 (g/g/s) by FSR) and is not disclosed in Patent Literatures 1 to 5 and 13, moreover it is preferable that the invention is applied to a water absorbing agent that is obtained by foaming polymerization, in particular by dispersing bubbles at the time of the polymerization, or by adding a foaming agent (particularly, an organic or inorganic carbonate salt and a urea) at the time of the polymerization or after the polymerization.

[Polymerizing Step]

The particulate water absorbing agent contains a water absorbent resin obtained by the polymerizing step as the base. In the polymerizing step, a polymerized gel is produced by polymerizing a monomer (hereinafter, referred to as the monomer in some cases) which can be converted into a water absorbent resin by polymerization. The polymerization method which can be used is not particularly limited, but examples thereof may include bulk polymerization, spraying polymerization, dropping polymerization, precipitation polymerization, aqueous solution polymerization (continuous aqueous solution polymerization), reversed-phase suspension polymerization, foaming polymerization, and the like. An aqueous solution polymerization in which the monomer can be used as an aqueous solution or a reversed-phase suspension polymerization in which the monomer can be used as an aqueous solution is preferable from the viewpoint of performance and ease of polymerization control. This production method makes it possible to sufficiently exert the effect (stabilization of physical properties) of the invention in a water absorbent resin obtained by aqueous solution polymerization. From this point of view, aqueous solution polymerization, in particular continuous aqueous solution polymerization is preferably used. In the continuous aqueous solution polymerization, continuous belt polymerization or continuous kneader polymerization can be suitably used.

The monomer is not particularly limited, but examples thereof may include an anionic unsaturated monomer such as (math) acrylic acid, an acid, 2-(meth)acrylamido-2-methylpropanesulfonic acid, 2-(meth)acryloylethanesulfonic acid, 2-(meth)acryloylpropanesulfonic acid, or 2-hydroxyethyl(math) acryloylphosphate and any salt thereof; a mercapto group-containing unsaturated monomer; a phenolic hydroxyl group-containing unsaturated monomer; a (meth) acrylamide, etc which are described in Patent Literature 13. These monomers may be used singly or two or more kinds thereof may be used by being appropriately mixed. The water absorbent resin is preferably a polyacrylic acid (salt)-based water absorbent resin from the viewpoint of performance of the water absorbent resin to be obtained and cost, and thus, it is preferable that the monomer uses acrylic acid and/or any salt thereof (for example, a salt of sodium, lithium, potassium, ammonium, amines, and the like, and a sodium salt is preferable among them from the viewpoint of cost) as the ma in component. The amount of acrylic acid and/or any salt thereof used is preferably 70% by mole or more, more preferably 80% by mole or more, still more preferably 90% by mole or more, and particularly preferably 95% by mole or more (upper limit is 100% by mole) based on the total monomer components (excluding internal crosslinking agent to be described later). The neutralization rate is preferably 40% by mole or more and 90% by mole or less and more preferably 50% by mole or more and 80% by mole or less in the polymer.

In a case in which the monomer described above is prepared as an aqueous solution in the polymerizing step, the concentration of the monomer in the aqueous solution (hereinafter, referred to as the "monomer solution" in some cases) is not particularly limited, but it is preferably within a range of from 10% by weight to 70% by weight and more preferably within a range of from 20% by weight to 60% by weight.

In addition, a solvent other than water may be used concurrently if necessary when conducting the aqueous solution polymerization or reversed-phase suspension polymerization described above. Incidentally, the kind of the solvent that is used concurrently is not particularly limited. Moreover, these monomers may contain a polymerization inhibitor or iron. The content of iron is preferably 5 ppm by weight or less and more preferably 1 ppm by weight or less based on the solid content of the monomer. In addition, the polymerization inhibitor is not particularly limited, and for example, methoxy phenols can be preferably used. In this case, the amount of the polymerization inhibitor used is 160 ppm by weight or less, and the details are disclosed in U.S. Pat. No. 7,049,366 and the like.

In the polymerizing step, for example, it is possible to use a radical polymerization initiator. The radical polymerization initiator is not particularly limited, and one kind or two or more kinds may be selected among those which are utilized in the polymerization of a usual water absorbent resin depending on the kind of the monomer to be polymerized, the polymerization conditions, and the like and used. For example, the polymerization initiator described in Patent Literature 13 can be widely used, and a persulfate salt is particularly preferable. In addition, the concurrent use of a reducing agent promotes the decomposition of these radical polymerization initiators, and thus it is possible to combine the two so as to use as a redox system initiator. The reducing agent is not particularly limited, and examples thereof may include sulfurous acid (hydrogen) (salt), L-ascorbic acid (salt), sulfinic acid such as 2-hydroxy-2-sulfinato acetic acid, and the like which are described in Patent Literature 13.

The amount of the radical polymerization initiator used is not particularly limited, but usually it is preferably from 0.001% by weight to 2% by weight and more preferably from 0.01% by weight to 0.15% by weight based on the amount of the monomer used.

In addition, it is possible to use an internal crosslinking agent in the polymerizing step it necessary. Examples of the internal crosslinking agent may include an internal crosslinking agent that is known in the prior art and has two or more polymerizable unsaturated groups and two or more reactive groups in one molecule. Examples of the internal crosslinking agent may include N,N'-methylenebis(meth)acrylamide, (poly)ethylene glycol di(meth)acrylate, (poly)propylene glycol di(meth)acrylate, trimethylolpropane tri(meth)acrylate, trimethylolpropane di(meth)acrylate, glycerin tri(meth)acrylate, glycerin acrylate methacrylate, ethylene oxide-modified trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallylamine, poly(meth)allyloxyalkane, (poly)ethylene glycol diglycidyl ether, glycerol diglycidyl ether, ethylene glycol, polyethylene glycol, propylene glycol, glycerine, 1,4-butanediol, pentaerythritol, ethylenediamine, ethylene carbonate, propylene carbonate, polyethyleneimine, glycidyl (meth)acrylate, and the like. These internal crosslinking agents may be used singly or two or more kinds thereof may be used.

Among them, it is preferable to use a compound having two or more polymerizable unsaturated groups as the internal crosslinking agent from the viewpoint of the water absorption characteristics of the water absorbent resin particles to be obtained etc, and the amount of the internal crosslinking agent used may be appropriately determined depending on the desired physical properties of the water absorbent resin, but usually the amount of the internal crosslinking agent used is preferably from 0.001% by mole to 5% by mole, more preferably from 0.005% by mole to 3% by mole, and still more preferably from 0.01% by mole to 1.5% by mole based on the monomer (total monomers).

In the polymerizing step, various kinds of foaming agents such as a carbonate (hydrogen) salt, carbon dioxide, an azo compound, or an inert organic solvent; a hydrophilic polymer such as starch-cellulose, any derivative of starch-cellulose, polyvinyl alcohol, polyacrylic acid (salt), or a crosslinked product of polyacrylic acid (salt); various kinds of surfactants; a chain transfer agent such as hypophosphorous acid (salt); or the like may be further appropriately added to the reaction system in a range in which the effect of the invention is not impaired (for example, various kinds of foaming agents are 30 parts by weight or less, a hydrophilic polymer is 30 parts by weight or less, and a chain transfer agent is 1 part by weight or less based on 100 parts by weight of the monomer) if necessary.

The polymerization temperature in the polymerizing step is not particularly limited, but usually it is preferably set to from 10° C. to 140° C. When the polymerization temperature is lower than 10° C., not only the productivity decreases as the polymerization time increases but also it is concerned that the physical properties of the water absorbent resin decreases. On the other hand, when it exceeds 140° C., it is concerned that the physical properties of the water absorbent resin decreases. The polymerization time is also not particularly limited, and it may be appropriately determined depending on the kinds of the monomer and the polymerization initiator, the polymerization temperature, and the like. In addition, the polymerization is conducted at a normal pressure or under pressure from the viewpoint of ease of the operation and the like, but it is also a preferred aspect to conduct this polymerization under reduced pressure in order to lower the boiling temperature at the time of the polymerization.

The continuous kneader polymerization or the continuous belt polymerization is suitably used for the production of the water absorbent resin in the invention. The water absorbent resin (particles) is obtained in high productivity as irregular crushed product having high physical properties by such a step, but it is difficult to fill such irregular crushed particles, there is a problem of deflection of or a decrease in physical properties at the time of filling, and such a problem of deflection or decrease is great particularly in large-scale continuous production, but the continuous kneader polymerization or the continuous belt polymerization can be suitably applied to the invention in order to solve such a problem. As such continuous kneader polymerization, for example, the continuous kneader polymerization described in U.S. Pat. Nos. 6,987,151, 6,710,141 and the like is suitably applied, and as the continuous belt polymerization, for example, the continuous belt polymerization described in U.S. Pat. Nos. 4,893,999, 6,241,928, US 2005-215734, and the like is suitably applied.

The present inventors have found out that it is possible to suppress the segregation of the water absorbent resin particles (particularly water absorbent resin particles having a high water absorbent speed) not only at the time of filling but also during transport by controlling the vibration force applied at the time of filling as described above, whereby they have completed the invention. According to a preferred embodiment of the invention, the water absorbent resin is a water absorbent resin that is obtained by polymerizing an aqueous solution of acrylic acid (salt) containing arbitrarily a surfactant and bubbles or a foaming agent. By having such an embodiment, it is possible to significantly increase the surface area of the particulate water absorbing agent (water absorbent resin) and to obtain a particulate water absorbing agent having a high free swell rate (PSR; 0.25 (g/g/s) or more), and also the particulate water absorbing agent is suitable for the filling method of the invention from the viewpoint of particle shape. In addition, according to a preferred embodiment of the invention, the particulate water absorbing agent is obtained by a production method including a step of belt polymerization. By having such an embodiment, an effect is exhibited that a water absorbing agent having a particle shape by which the effect of the invention is easily obtained is obtained.

Here, suitable bubbles are formed by an inert gas, in particular a nitrogen gas, and as a suitable foaming agent, a carbonate salt or urea, in particular a carbonate salt, a monovalent and/or a divalent inorganic carbonate salt or a hydrogen carbonate salt (for example, sodium carbonate, magnesium carbonate, or sodium hydrogen carbonate) is used. The foaming agent can be added to the aqueous monomer solution, the solution in the polymerization, the hydrogel after the polymerization, or the like, but it is preferably added to the aqueous monomer solution.

The content of the bubbles is a gas amount to expand by preferably from 1.01 times to 10 times and more preferably about from 0.02 times to 2 times based on the aqueous monomer solution, and the content of the foaming agent is appropriately determined to be about from 0.1% by weight to 10% by weight based on the aqueous monomer solution. The surfactant can be used in order to control the amount or size of the bubbles, the amount thereof used is appropriately determined to be about from 0.001% by weight to 1% by weight based on the aqueous monomer solution.

The preferred surface tension (described in WO 2005/075070 A) of the particulate water absorbing agent is preferably 50 (mN/m) or more, more preferably 60 (mN/m) or more, still more preferably 65 (mN/m) or more, and particularly preferably 70 (mN/m) or more in consideration of the return amount when used in a paper diaper and the like, and the upper limit is usually about 73 (mN/m). The surface tension can be controlled by the kind and amount of the surfactant used, and the surfactant may have a polymerizable functional group or a reactive functional group (glycidyl group or the like). Specifically, the surfactants described in Patent Literatures 7 to 12 and the like, in particular, nonionic or anionic surfactants are preferable.

Incidentally, examples of the method for obtaining a suitable water absorbent resin having a high water absorbent speed may include granulation of fine powder (for example, the method described in U.S. Pat. No. 5,002,986), grain refining of particles (substantially 300 μm or less and further 200 μm or less), foaming at the time of polymerization, foaming at the time of drying, fine crushing of the polymer gel, etc and the method is appropriately selected, but as described above, foaming at the time of polymerization and foaming at the time of drying are preferable, in particular foaming at the time of polymerization is applied.

The foaming method is described in Patent Literatures 7 to 12, in addition to this, the following techniques to use the following foaming agents as the foaming agent used in the monomer in the foaming polymerization are known, specifically, a technique to use a carbonate salt (Patent Literatures 14 to 22), a technique to use an organic solvent (Patent Literatures 18 and 19), a technique to use a polyvinyl monomer (Patent Literature 23), a technique to use an inert gas (Patent Literatures 24 to 26), a technique to use an azo compound (Patent Literatures 27 and 28), a technique to use an insoluble inorganic powder (Patent Literature 29), and the like are known, and also a technique to foam and crosslink after the polymerization (Patent Literature 30) and the like are proposed. Furthermore, a technique to use water-insoluble particles in the polymerization (Patent Literature 31) can also be applied. In addition, a technique to control the physical properties by gel grinding (Patent Literature 32) can also be applied.

(Patent Literature 14) U.S. Pat. No. 5,118,719
(Patent Literature 15) U.S. Pat. No. 5,154,713
(Patent Literature 16) U.S. Pat. No. 5,314,420
(Patent Literature 17) U.S. Pat. No. 5,399,591
(Patent Literature 18) U.S. Pat. No. 5,451,613
(Patent Literature 19) U.S. Pat. No. 5,462,972
(Patent Literature 20) WO 95/02002
(Patent Literature 21) WO 2005/063313
(Patent Literature 22) WO 94/022502
(Patent Literature 23) U.S. Pat. No. 4,703,067
(Patent Literature 24) WO 97/017397
(Patent Literature 25) WO 00/052087
(Patent Literature 26) U.S. Pat. No. 6,107,358
(Patent Literature 27) U.S. Pat. No. 5,856,370
(Patent Literature 28) U.S. Pat. No. 5,985,944
(Patent Literature 29) WO 2009/062902
(Patent Literature 30) EP 1,521,601
(Patent Literature 31) US 2007/0225422
(Patent Literature 32) WO 2011/126079

[Drying Step]

By the drying step, the polymer gel (also called: hydrogel-like polymer) obtained in the polymerizing step described above is dried. In the drying step, the polymer gel that is obtained in the polymerizing step described above and has a moisture content of from 15% by weight to 70% by weight is dried although it is not limited thereto. It is preferable that the polymer gel obtained in the polymerizing step is usually subjected to the drying step in a particulate state of about from 0.1 mm to 5 mm.

The drying method in the drying step is not particularly limited, but a method, such as hot air drying and azeotropic dehydration, to use a usual dryer and a heating furnace can be widely employed. More specifically, examples of the drying device may include a conductive heat transfer-type dryer, a radiation heat transfer-type dryer, a hot air heat transfer-type dryer, a dielectric heating dryer, and the like. A hot air heat transfer-type dryer (hereinafter, hot air dryer) and further a through-flow band-type dryer are preferable from the viewpoint of the fastness of drying. The drying temperature is appropriately determined in a range of from 70° C. to 250° C., further from 100° C. to 200° C., and from 150° C. to 190° C., and the drying time is about from 1 minute to hours and about from 5 minutes to 1 hour.

Suitable drying methods are described in WO 2011/025013, WO 2011/025012, WO 2011/111657, WO 2011/111657, WO 2011/15540, WO 2011/136301, WO 2008/037676, WO 2006/100300, and the like.

[Pulverizing Step]

The pulverizing method is not particularly limited, and a method known in the prior art can be employed. The pulverizing method is appropriately selected, and the pulverizing methods described in US 2006-024755, WO 2011/034147, HO 2011/034146, and the like are used. Among these, a roll mill or a roll granulator can be suitably used from the viewpoint of the particle size control, and the water absorbent resin can be pulverized using a roll mill or a roll granulator of one stage, preferably multistage, more preferably from two to five stages and applied.

[Classifying Step]

The classifying step of the water absorbent resin is an arbitrary step and can be carried out not only before the surface crosslinking but also after the surface crosslinking. Hence, the classifying step can be applied preferably before the surface crosslinking and/or after the surface crosslinking, more preferably before the surface crosslinking, and still more preferably after the surface crosslinking as well. Incidentally, the classification after the surface crosslinking is also referred to as the sizing step. The classifying method is not particularly limited, and it is exemplified in U.S. Pat. No. 6,164,455, HO 2006/074816, WO 2008/037672, WO 2008/037673, WO 2008/037675, WO 2008/123477, and the like. Among these, in particular the sieve classification is applied, and the number of sieves is appropriately determined in about from two to five stages.

[Surface Crosslinking Step]

The surface crosslinking step is a step of crosslinking the vicinity of the surface of the particulate water absorbent resin obtained in the classifying step described above using a surface crosslinking agent. By this step, a particulate water absorbing agent having a crosslinked surface is obtained. A particulate water absorbent resin is a water-swellable crosslinked polymer and has a crosslinked structure in the (particle) inside, but it is preferable that the surface of the water absorbent resin (particles) which can be used in the invention is crosslinked and the crosslinking density of the surface or the vicinity of the surface is higher than the inside.

The aggregation of the particulate water absorbent resin can be suppressed by such a surface crosslinking step. Incidentally, the "vicinity of the surface" usually means the surface layer part having a thickness of several tens of μm or the surface layer part having a thickness of 1/10 of the entire thickness, but this thickness is appropriately determined depending on the purpose. Such surface crosslinking of the water absorbent resin may be (1) the surface crosslinking by an organic surface crosslinking agent and/or a water-soluble inorganic surface crosslinking agent which are exemplified as a surface crosslinking agent later, (2) the surface cross linking conducted by crosslinking polymerization of a crosslinking monomer on the surface (for example, disclosed in U.S. Pat. No. 7,201,941), or (3) the radical surface crosslinking by a peraulfate salt and the like (for example, disclosed in U.S. Pat. No. 4,783,510).

Hereinafter, a surface crosslinking method using a surface crosslinking agent will be described as a preferred crosslinking method.

As the surface crosslinking agent used in the surface crosslinking step, a surface crosslinking agent known in the prior art is suitably used. For example, a polyhydric alcohol or an epoxy compound or an alkylene carbonate compound described in Patent Literature 13 are used, and at least one kind of compound selected from the group consisting of a polyhydric alcohol compound, an epoxy compound, a polyvalent amine compound, or any salt thereof, an alkylene carbonate compound, and an oxazolidinone compound is suitable. Furthermore, one kind or two or more kinds of dehydrated and esterified reactive surface crosslinking agents selected from an oxazolidinone compound, an alkylene carbonate compound, a polyhydric alcohol compound, or an oxetane compound are preferable for the surface crosslinking in the invention. The amount of the surface crosslinking agent used is preferably 0.001 part by mass or more and 5 parts by mass or less, more preferably 0.01 part by mass or more and 4 parts by mass or less, and still more preferably 0.05 part by mass or more and 3 parts by mass or less based on 100 parts by mass of the solid content of the water absorbent resin.

In the surface crosslinking step, an organic acid (lactic acid, citric acid, p-toluenesulfonic acid) or any salt thereof, an acid material such as an inorganic acid (phosphoric acid, sulfuric acid, sulfurous acid) or any salt thereof, a base material such as sodium hydroxide or sodium carbonate, a polyvalent metal salt such as aluminum sulfate, water-insoluble fine particles, and the like may be further used concurrently at preferably from 0% by weight to 10% by weight, more preferably from 0% by weight to 5% by weight, and still more preferably from 0% by weight to 1% by weight based on the water absorbent resin in addition to the surface crosslinking agent described above.

In the surface crosslinking step, it is preferable to use water as a solvent upon mixing the particulate water absorbent resin and the surface crosslinking agent. The amount of water used is preferably more than 0 parts by weight and 20 parts by weight or less and more preferably in a range of from 0.5 parts by weight to 10 parts by weight based on 100 parts by weight of the solid content of the particulate water absorbent resin although it is also dependent on the kind of the water absorbent resin, the particle size of the particulate water absorbent resin, the moisture content, and the like. A hydrophilic organic solvent may be used concurrently if necessary upon mixing the particulate water absorbent resin and the surface crosslinking agent. The amount of the hydrophilic organic solvent used is preferably from 0 parts by weight to 20 parts by weight and more preferably in a range of from 0 parts by weight to 10 parts by weight based on 100 parts by weight of the solid content of the particulate water absorbent resin although it is also dependent on the kind of the water absorbent resin, the particle size of the particulate water absorbent resin, the moisture content, and the like.

Upon conducting the surface crosslinking, a method is preferable in which a surface crosslinking agent solution containing the surface crosslinking agent and the solvent is mixed with the particulate water absorbent resin by being sprayed by a spray or the like or added dropwise and a method is more preferable in which the solution is mixed with the particulate water absorbent resin by being sprayed. The size of the droplets to be sprayed is preferably in a range of from 0.1 µm to 300 µm and more preferably in a range of from 0.1 µm to 200 µm as an average particle size.

In the surface crosslinking step, the mixture of the particulate water absorbent resin and the surface crosslinking agent solution can be subjected to the surface crosslinking even at room temperature. However, from the viewpoint of the promotion of the reaction and the removal of the added water and solvent, it is preferable to crosslink the vicinity of the surface of the particulate water absorbent resin after mixing the particulate water absorbent resin and the surface crosslinking agent and further subjecting the mixture to a heat treatment. In the heat treatment, the treatment temperature is preferably 80° C. or higher although it also depends on the surface crosslinking agent to be selected. The treatment temperature (heat medium temperature or material temperature/particularly the heat medium temperature) is preferably in a range of from 100° C. to 250° C., more preferably in a range of from 150° C. to 250° C. (particularly suitable for the dehydrated and esterified reactive surface crosslinking agent). The heating time is preferably in a range of from 1 minute to 2 hours. A preferred example of the combination of the heating temperature and the heating time is at 180° C. for from 0.1 hours to 1.5 hours and at 200° C. for from 0.1 hours to 1 hour.

As the heating device used for conducting the heat treatment, a known dryer or a heating furnace is used. For example, a conductive heat transfer-type, a radiation heat transfer-type, a hot air heat transfer-type, or a dielectric heating-type dryer or heating furnace is suitable. Specific examples thereof may include a belt-type, a groove-type stirring-type (for example, a paddle dryer), a screw-type, a rotary, a disk-type, a kneading-type, a fluidized bed-type, an air flow-type, an infrared-type, or an electron beam-type dryer or heating furnace.

[Cooling Step]

The cooling step is an arbitrary step which carried out after the surface crosslinking, and for example, it is a step in which the particulate water absorbing agent that has been heated in the surface crosslinking step described above in order to crosslink the vicinity of the surface is cooled before being subjected to the sizing step to be described later. The cooling temperature is not particularly limited, but the particulate water absorbing agent may be cooled to preferably from 0° C. to 100° C., more preferably from 30° C. to 90° C., and still more preferably from 30° C. to 70° C. The cooling device used in this cooling step is not particularly limited, but the cooling unit is not particularly limited, but it is exemplified in U.S. Pat. No. 6,378,453, WO 2011/024971, and the like.

[Step of Adding Additive]

Examples of the additive to be added in the adding step may include the following (A) a deodorant component (preferably a plant component), (B) a polyvalent metal salt, (C) inorganic particles (including (D) a composite hydrous oxide), (E) other additives, and the like. As the amount thereof added is preferably from 0.001 parts by mass to 10 parts by mass, more preferably from 0.001 parts by mass to 5 parts by mass, and still more preferably in a range of from 0.002 parts by mass to 3 parts by mass based on 100 parts by mass of the water absorbent resin.

(A) Deodorant Component

It is possible to blend a deodorant component, preferably a plant component into the particulate water absorbing agent obtained by the production method of the invention so that the particulate water absorbing agent exerts an odor eliminating effect. As the plant component, at least one kind of compound selected from a polyphenol, flavone and flavones, or caffeine is preferable and at least one kind of compound selected from tannin, tannic acid, oak apple, or nutgall and gallic acid is still more preferable.

(B) Polyvalent Metal Salt

A polyvalent metal salt can be blended into the particulate water absorbing agent obtained by the production method of the invention for the purpose of improving the liquid permeability or the powder fluidity, in particular the powder fluidity at the time of moisture absorption. The preferred amount of this polyvalent metal salt is as above.

Examples of the preferred polyvalent metal salt may include a polyvalent metal salt of an organic acid and an inorganic polyvalent metal salt. Specific examples of the inorganic polyvalent metal salt may include polyvalent metal salts and the like described in Patent Literature 6. Examples of the polyvalent metal salt of an organic acid may include an aluminum salt or a calcium slat of lactic acid, acetic acid, and the like. Furthermore, it is preferable to use a salt having this crystal water from the viewpoint of solubility in the liquid to be absorbed such as urine as well. As the particularly preferred ones, an aluminum compound, among them, aluminum chloride, polyaluminum chloride, aluminum sulfate, aluminum nitrate, aluminum potassium bis(sulfate), aluminum sodium bis(sulfate), potassium alum, ammonium alum, sodium alum, and sodium aluminate are preferably, aluminum sulfate is particularly preferably, and a powder of hydrous crystal such as aluminum sulfate octadecahydrate and aluminum sulfate teradeca- to octadecahydrate can be most suitably used. These may be used singly or two or more kinds thereof may be used concurrently. In addition, the polyvalent metal salt is preferably used in a solution state, in particular in an aqueous solution state from the viewpoint of handling property and mixing property with the particulate water absorbing agent.

In addition, the usable polyvalent metal salt of an organic acid and the mixing method thereof are exemplified in U.S. Pat. No. 7,282,262. As the polyvalent metal salt of an organic acid having 7 or more carbon atoms in the molecule which can be used in the invention, a metal salt other than an alkali metal salt of a fatty acid, a petroleum acid, a polymeric acid, and the like.

(C) Inorganic Particles

It is possible to blend inorganic particles, in particular water-insoluble inorganic particles into the particulate water absorbing agent obtained by the production method of the invention in order to prevent blocking at the time of moisture absorption. Specific examples of the inorganic particles used in the invention may include a metal oxide such as silicon dioxide or titanium oxide; silicic acid (salt) such as natural zeolite or synthetic zeolite; kaolin; talc; clay; bentonite, calcium phosphate, hydrotalcite, and the like. Among these, silicon dioxide and silicic acid (salt) are more preferable and silicon dioxide and silicic acid (salt) having an average particle size that is measured by the Coulter counter method of from 0.001 μm to 200 μm are still more preferable.

(E) Other Additives

For example, a chelating agent, an antiseptic agent, an antibacterial agent, a perfume, various kinds of inorganic powders, a foaming agent, a pigment, a dye, hydrophilic short fibers, a fertilizer, an oxidizing agent, a reducing agent, aqueous salts, and the like can be added to the particulate water absorbing agent obtained by the production method of the invention if necessary in a range in which the effect of the invention is not impaired. The amount of these other additives added can be set to, for example, preferably 30 parts by mass or less and more preferably 10 parts by mass or less based on 100 parts by mass of the particulate water absorbing agent. By this addition, various functions can be imparted.

In addition, there are the following ones as another embodiment of the additive.

(Additive)

The particulate water absorbing agent may contain polyamine polymer, a polyvalent metal (salt), and water-insoluble fine particles at a proportion of preferably from 0.001 parts by weight to 5 parts by weight and more preferably from 0.01 parts by weight to 3 parts by weight based on 100 parts by weight of the particulate water absorbing agent. In particular, it is preferable that polyamine polymer, a polyvalent metal (salt), and water-insoluble fine particles are present on the surface of the particulate water absorbing agent.

As the polyvalent metal (salt), a polyvalent metal salt such as aluminum sulfate, in particular a water-soluble polyvalent metal salt is preferable, and the techniques described in U.S. Pat. No. 7,179,862, EP 1,165, 631, U.S. Pat. Nos. 7,157,141, 6,831,142, US2004/176557. US2006/204755, US2006/73969, US 2007/106013, and the like are applied.

As the water-insoluble fine particles, water-insoluble inorganic fine particles are preferable, and the particle size thereof is preferably 300 μm or less, more preferably 100 μm or less, and still more preferably μm or less. Specifically, known water-insoluble fine particles such as amorphous silica (for example, Aerosil 200 (manufactured by NIPPON AEROSIL CO., LTD.)) can be used.

Polyamine polymer is exemplified in WO 2006/082188, WO 2006/082189, WO 2006/082197, and the like. Here, polyamine polymer is not particularly limited, but those which are soluble in water and have a weight average molecular weight of 3.000 or more and further an amine value of from 1 (mol/kg) to 30 (mol/kg) are more preferable.

In addition, the invention can be effective for the particulate water absorbing agent containing a polyvalent metal salt such as aluminum sulfate or inorganic particles as well. It is believed that this is because the suppression of blocking due to the polyvalent metal salt or inorganic particles can promote the relaxation of the uneven distribution due to vibration.

(P) Chelating Agent

The particulate water absorbing agent used in the invention may contain a chelating agent. The step of mixing the chelating agent is not particularly limited, but it is preferable to mix the chelating agent into the monomer or the monomer solution. As the chelating agent, various polymer chelating agents or non-polymer chelating agents can be exemplified, but preferably an acid group-containing non-polymer chelating agent such as pentasodium ethylenediamine tetra(methylene phosphonate), and more preferably a phosphorus acid group-containing non-polymer chelating agent or a carboxylic acid group-containing non-polymer chelating agent is used, and a non-polymer chelating agent containing such an acid group in the molecule by preferably from 2 to 100, more preferably from 2 to 50, and still more preferably from 2 to 10 is used. In addition, amino carboxylic acid or amino phosphoric acid which has nitrogen in the chelating agent is preferable, and examples thereof may include the chelating agents described in U.S. Pat. No. 6,599,989 or WO 2008/090961. The amount of the chelating agent used in the particulate water absorbing agent is preferably from 5 ppm by mass to 10,000 ppm by mass and more preferably from 10 ppm by mass to 1000 ppm by mass. An effect of preventing coloration of the water absorbent resin is exhibited as the chelating agent is contained.

(G) Surfactant

As the surfactant, the surfactants described in U.S. Pat. No. 6,107,358 can be applied to the invention. The amount of the surfactant used in the particulate water absorbing agent is preferably from 10 ppm by mass to 1000 ppm by mass.

[Sizing Step]

The method for producing a particulate water absorbing agent may further include a sizing step described in Patent Literature 13.

[Granulating Step]

The method for producing a particulate water absorbing agent may further include a step of recovering a fine powder or a granulating step described in Patent Literature 13.

The granulating step is a step of obtaining the granulated particles by adding an aqueous solution to a fine powder generated in the above respective steps or the water absorbent resin containing the fine powder. The entire fine powders obtained in the production of particulate water absorbing agent can be subjected to this granulating step. The granulated particles are composed of a plurality of fine powders. The average particle size of the granulated particles is preferably 20 mm or less, more preferably from 0.3 mm to 10 mm, and still more preferably from 0.35 mm to 5 mm.

According to a preferred embodiment, it is possible to prepare a particulate water absorbing agent in the manner described above. Hereinafter, a preferred embodiment of the particulate water absorbing agent to be filled will be further described.

<Particulate Water Absorbing Agent>

[Particle Size Distribution](ERT 420.2-02)

The mass average particle size (D50) of the particulate water absorbing agent defined by JIS standard sieve classification is preferably from 200 µm to 800 µm, more preferably from 200 µm to 450 µm, still more preferably from 220 µm to 430 µm, and particularly preferably from 250 µm to 400 µm from the viewpoint of handling at the stage of (III) above and wearing feel of the absorbent article to be obtained.

In addition, the effect of the invention can be efficiently exerted in a case in which the particulate water absorbing agent has a specific particle size distribution. As the preferred particle size distribution, the proportion of the particles which are classified into the upper and lower limit of 850 µm to 150 µm (JIS standard sieve; defined in Z8801-1 (2000)) is preferably from 90% by weight to 100% by weight, more preferably from 95% by weight to 100% by weight, and still more preferably from 98% by weight to 100% by weight based on the entire particle water absorbing agent. Moreover, the particulate water absorbing agent which passes through a 150 µm mesh is preferably less than 5% by weight and more preferably less than 1% by weight. The particulate water absorbing agent which passes through a 150 µm mesh is classified by a JIS standard sieve (defined in Z8801-1 (2000)).

[Logarithmic Standard Deviation ($\sigma\zeta$)]

The particle size distribution of the particulate water absorbing agent is preferably in a specific range in order to efficiently exert the effect of the invention, and the logarithmic standard deviation ($\sigma\zeta$) is preferably from 0.20 to 0.50, more preferably from 0.25 to 0.45, and still more preferably from 0.30 to 0.40. It is possible to efficiently fill the particulate water absorbing agent when the logarithmic standard deviation is in such a range. In addition, it is easy to exert the effect of the sampling method of the invention. In addition, it can be said that it is a preferred range in order to improve the liquid permeability or the water absorbent speed as a physical property. Incidentally, the logarithmic standard deviation of the particle size distribution or the mass average particle size is defined in US 2006-0204755.

[AAP] (ERT 442.2-02)

The absorbency against pressure (AAP) of the particulate water absorbing agent with respect to saline at a load of 4.8 kPa that is defined in ERT 442.2-02 is preferably 15 (g/g) or more. An absorbent article such as a diaper using such a particulate water absorbing agent favorably absorbs the body fluids and the like. The AAP of the particulate water absorbing agent is more preferably 20 (g/g) or more, still more preferably 22 (g/g) or more, further still more preferably 23.5 (g/g) or more, particularly preferably 24 (g/g) or more, and most preferably 26 (g/g) or more.

Incidentally, although the reason is not clear, it has been demonstrated that the filling method of the invention is effective in a case in which the AAP is great. The uneven distribution of the fine powders to the surface layer part is relaxed by the vibration filling of the invention, and thus the deflection of the AAP caused by the uneven distribution of the fine powders decreases. The strict quality control is required to a particulate water absorbing agent having a great AAP, but the stability degree of quality increases as the deflection of the AAP decreases. Meanwhile, the upper limit of the absorbency against pressure is not particularly limited since the absorbent article has higher physical properties as the absorbency against pressure is higher, but it is believed that the upper limit of this absorbency against pressure is about 35 (g/g) from the viewpoint of being difficult to produce and a steep rise in cost. This absorbency against pressure with respect to saline at a load of 4.8 kPa is also referred to as the AAP (4.8 kPa) or simply the AAP in the invention.

In addition, it is desirable to increase the surface area of the particulate water absorbing agent in order to increase the PSR. In order to increase the surface area, it is desirable to contain a great amount of particulate water absorbing agent which has a small particle size to a certain extent. However, it is difficult to increase the AAP or the SFC when the amount of the fine powders (particularly particles having a particle size of less than 150 µm) increases.

According to the filling method of the invention, the fine powders of which the physical properties are difficult to be controlled can be distributed to each lot without segregation and thus a particulate water absorbing agent having uniform quality is obtained, as a result, the invention is a breakthrough invention.

[SFC]

The saline flow conductivity (SFC) is a value indicating the liquid permeability of the particulate water absorbing agent at the time of swelling. This saline flow conductivity is referred to as the liquid permeability. It indicates that the particulate water absorbing agent exhibits higher liquid permeability as the value of this saline flow conductivity (SFC) is greater.

The saline flow conductivity (SFC) of the particulate water absorbing agent is preferably 20 ($\times 10^{-7} \cdot cm^3 \cdot s \cdot g^{-1}$) or more. An absorbent article such as a diaper using such a particulate water absorbing agent favorably absorbs the body fluids and the like. It is preferable that the SFC is preferable 30 ($\times 10^{-7} \cdot cm^3 \cdot s \cdot g^{-1}$) or more, 35 ($\times 10^{-7} \cdot cm^3 \cdot s \cdot g^{-1}$) or more, 40 ($\times 10^{-7}$ $cm^3 \cdot s \cdot g^{-1}$) or more, 45 ($\times 10^{-7} \cdot cm^3 \cdot s \cdot g^{-1}$) or more, and 45.5 ($\times 10^{-7} \cdot cm^3 \cdot s \cdot g^{-1}$) or more in this order. In the absorbent articles containing such a particulate water absorbing agent, the absorption rate of urine is properly maintained and the occurrence of leakage is also suppressed even in a case in which the concentration of the particulate water absorbing agent contained in the article is 30% by weight or more and more specifically 50% by weight or more.

(CRC)

The centrifuge retention capacity (CRC) of the particulate water absorbing agent with respect to saline is preferably 5 (g/g) or more. This centrifuge retention capacity is more preferably 15 (g/g) or more and still more preferably 25 (g/g) or more. The upper limit of the centrifuge retention capacity is not particularly limited, but it is about 60 (g/g), 45 (g/g), or 40 (g/g) in reality.

[FSR]

The free swell rate (FSR) of the particulate water absorbing agent is preferably 0.20 (g/g/s) or more, more preferably 0.24 (g/g/s) or more, still more preferably 0.25 (g/g/s) or more, and particularly preferably 0.30 (g/g/s) or more. The upper limit of the FSR is not particularly limited, but it is about 1.00 (g/g/s), 0.50 (g/g/s), or 0.45 (g/g/s) in reality.

[Particle Shape]

It is preferable that the particle shape of the particulate water absorbing agent (water absorbent resin) is not a true sphere (average sphericity=1.0), and a spherical shape, a substantially spherical shape, an irregular crushed shape, or a granulated product (aggregate) thereof is suitable, and the particulate water absorbing agent may be a foamed product of those particles. Incidentally, the average sphericity is referenced to the measuring method described in WO 2008/009599.

However, the particulate water absorbing agent preferably has an irregular crushed shape or is a granulated product thereof from the viewpoint of exerting the effect of the sampling method of the invention. In addition, it is preferable that the particulate water absorbing agent has an irregular crushed shape or is a granulated product thereof from the viewpoint of the free swell rate or fixing property to the pulp. Incidentally, as the particulate water absorbing agent (water absorbent resin) to be filled has an irregular crushed shape, the water absorbent resin of the particulate water absorbing agent to be filled to be described later also has the same shape. In other words, the filled particulate water absorbing agent is constituted by containing a water absorbent resin, and the water absorbent resin is irregular crushed particles. Incidentally, it is preferable that the water absorbent resin is not produced by the reversed-phase suspension polymerization in order to fabricate these irregular crushed particles.

Incidentally, the irregular crushed particles refer to particles which do not have a specific shape and have a surface formed in irregular concave and convex shapes.

[Bulk Specific Gravity]

The bulk specific gravity (bulk density) (JIS K 3362) of the particulate water absorbing agent is usually from 0.45 (g/ml) to 0.75 (g/ml), preferably from 0.50 (g/ml) to 0.70 (g/ml), and more preferably from 0.55 (g/ml) to 0.65 (g/ml). It is preferable that the bulk specific gravity is 0.50 (g/ml) or more from the viewpoint of being able to produce a particulate water absorbing agent having a high free swell rate. It is suitable that the bulk specific gravity is 0.70 (g/ml) or less from the viewpoint of obtaining a desired free swell rate. In addition, according to the filling method of the invention, the bulk specific gravity is preferably in the above range since an effect of suppressing the segregation during transport is remarkably exhibited. In addition, according to the filling method of the invention, it is possible to efficiently fill a particulate water absorbing agent having a low bulk specific gravity.

Incidentally, the bulk specific gravity is measured as follows.

The bulk specific gravity is measured using a bulk specific gravity measuring instrument (manufactured by Kuramochi Scientific Instrument Co., Ltd.) in conformity with JIS K 3362. Into a funnel with a closed damper, 100.0 g of a particulate water absorbing agent that is thoroughly mixed in order to eliminate the bias due to the particle size is introduced, the damper is then promptly opened, and the particulate water absorbing agent is dropped into a receiver (weight W9 (g)) having an inner capacity of 100 ml. The particulate water absorbing agent which has raised from the receiver is scraped off with a glass rod, the weight (weight W10 (g)) of the receiver which contains the particulate water absorbing agent is then accurately weighed to 0.1 g, and the bulk specific gravity is calculated by the following Equation. Incidentally, the temperature and relative humidity of the environment in which the measurement is conducted are set to 24.2° C. and 43% RH, respectively.

Bulk specific gravity (g/ml)=($W10$ (g)–$W9$ (g))/100

<Filling Method>

Subsequently, a method for filling the "particulate water absorbing agent" according to the embodiment of the invention described above in a filling container will be described. The method for filling a particulate water absorbing agent of the invention (in the present specification, also simply referred to as the "filling method of the invention") includes a filling step of filling a particulate water absorbing agent into a filling container and a vibrating step of vibrating the filling container at the outside of the filling container, and in which the vibrating step is conducted at least one time between the start and the end of the filling step and the vibration condition in the vibrating step satisfies the following conditions (a) and (b).

(a) Vibration by a vibrating body in contact with the filling container has a vertical directional component and a vibrational angle is within 90°±30° and (b) total amplitude at no load and a vibration frequency at no load of the vibrating body are set so as to satisfy the following Equation 1-1 and Equation 2 or Equation 1-2 and Equation 2.

[Mathematical Formula 5]

1≤acceleration (G)≤13 in a case in which final filling amount of particulate water absorbing agent per filling container: $W2$≥100 kg  (Equation 1-1)

1≤acceleration (G)≤15 in a case in which final filling amount of particulate water absorbing agent per filling container: $W2$<100 kg  (Equation 1-2)

[Mathematical Formula 6]

27.0≤vibration index≤44.0  (Equation 2)

Incidentally, the acceleration and the vibration index are a value calculated by the following Equation 3 and Equation 4, respectively.

[Mathematical Formula 7]

$$\text{Acceleration}[G] = \frac{\text{total amplitude at no load [mm]} \times (2\pi \times \text{vibration frequency at no load [Hz]})^2}{2 \times 1000 \times 9.8} \quad \text{(Equation 3)}$$

[Mathematical Formula 8]

$$\text{Vibration index} = 42 - 0.29 \times \text{vibration frequency at no load[Hz]} + 1.24 \times \text{acceleration}[G] \quad \text{(Equation 4)}$$

By the configuration described above, it is possible to significantly decrease the variation of water absorption physical property values of the respective final products (absorbent articles), and thus it is possible to provide a technique in which a decrease in physical properties is suppressed or consumer complaints are diminished.

As described above, the filling method of the invention includes a filling step of filling a particulate water absorbing agent into a filling container and a vibrating step of vibrating the filling container at the outside of the filling container.

(Start and End of Filling Step)

The "start of the filling step" is the time point at which the particulate water absorbing agent is begun to be introduced into the filling container, more accurately, it is the time point at which the particulate water absorbing agent has entered the internal space of the filling container for the first time, and the "end of the filling step" is the time point at which it has been confirmed that the particulate water absorbing agent in the container is in a predetermined amount (final filling amount W2).

For example, in the case of conducting the filling in the following procedure, the beginning of (2) corresponds to the "start of the filling step" and the finish of (5) corresponds to the "end of the filling step".

(1) The filling container is set to the filling location, (2) the outlet of the filling hopper is opened and the particulate water absorbing agent enters the filling container, (3) the particulate water absorbing agent is deposited in the filling container, (4) the filling is stopped, (5) the particulate water absorbing agent is supplied while being adjusted so as to be in a predetermined amount, (6) the lid is put on the filling container, and (7) the filling container is sent to the next step.

FIG. 1 is a view illustrating an example of a filling apparatus 2 usable in the invention.

In the case of describing the filling step with reference to FIG. 1, the time point at which the particulate water absorbing agent has passed through a discharge port 18 is the start and the time point at which it has been confirmed that the particulate water absorbing agent is filled in a filling container 16 in a predetermined amount is the end. Hence, the stage to attach the filling container 16 to the discharge port 18 and the stage to detach the filling container 16 from the discharge port 18 are not included in the filling step.

Incidentally, the predetermined amount is not required to be the only amount, but it is an amount that is controlled in a width within ±5%, preferably within ±3%, and more preferably within ±1% of the desired value, and also it may be the mass and/or the capacity. In other words, it may be the weight represented by "kg" or the volume represented by "L".

(Particulate Water Absorbing Agent to be Supplied)

The temperature of the particulate water absorbing agent to be supplied in the filling step is preferably 30° C. or higher and more preferably 35° C. or higher. The aggregation of the particles is suppressed and the vibration effect increases when the temperature is moderate, but the temperature is preferably 90° C. or lower and more preferably 70° C. or lower from the viewpoint of maintaining the physical properties of the particulate water absorbing agent. Hence, according to a preferred embodiment of the filling method of the invention, the temperature of the particulate water absorbing agent in the vibrating step is from 30° C. to 70° C.

(Filling Container)

Examples of the filling container 16 may include a flexible container bag, a container, a portable silo, a paper bag, and the like, and the filling container 16 may be a silo which is exemplified in HO 2005/077786, for example.

The capacity of the filling container is appropriately designed from the final filling amount (W2) and the bulk density (BD) that is the mass per unit volume, and it is not preferable that the capacity is 1.05 or less times the value of W2+BD since it is not possible to put the lid in some cases. The upper limit may be appropriately set in consideration of the cost of the filling container, the space of the storage location, the transport cost, and the like, and 1.5 or less times is usually sufficient.

Specifically, it is 20 m³ or less, preferably from 0.1 m³ to 10 m³, more preferably 700 liters or more and 2,500 liters or less, and still more preferably from 1,000 liters to 2,000 liters. However, as described above, the excessive capacity does not cause any particular problem. Incidentally, as the specific examples of the excessive capacity, there is a case in which a particulate water absorbing agent is filled in a plurality of filling containers in a predetermined amount and finally the particulate water absorbing agent that is less than the predetermined amount is filled in the filling container without changing the size of the filling container, for example.

The flexible container bag preferably has a multilayer structure of two or more layers. The material constituting the inner layer is not particularly limited, but it is preferably a material capable of preventing leakage or moisture absorption of the particulate water absorbing agent. As the material of the inner layer, a material which exhibits moisture barrier properties can be employed. Specific examples thereof may preferably include polyethylene (PE), polypropylene (PP), polyethylene terephthalate (PET), polyvinyl chloride (PVC), an aluminum laminated material, an aluminum deposited material, and the like.

In addition, the material constituting the outer layer is also not particularly limited, woven fabrics and the like which have an excellent strength are preferably used. In addition, the material constituting the outer layer is not particularly limited as long as it has properties as described above, and specific examples thereof may preferably include polypropylene and the like.

The relative humidity in the filling container is preferably 65% RH or less and more preferably 60% RH or less and preferably 30% RH or more. The relative humidity can be adjusted when preparing the supply to be described later. In addition, the temperature in the filling container is preferably 20° C. or higher and more preferably 30° C. or higher and preferably 70° C. or lower and more preferably 60° C. or lower. In addition, the temperature of the surroundings of the filling container (filling apparatus) is preferably from 20° C. to 30° C.

(Preparation of Supply)

It is preferable that the supplying step is carried out after filling dry air to the inside of the filling container before starting the filling step. The dry air in the invention refers to a gas (air and the like) having a dew point of −10° C. or lower. The dew point is preferably −10° C. or lower, more preferably −15° C. or lower, and still more preferably −20° C. or lower from the viewpoint that the excellent physical properties of the particulate water absorbing agent are stably maintained and the blocking can be prevented. In addition, the lower limit value of the dew point is −100° C. In addition, the temperature of dry air is preferably from −10° C. to 100° C., more preferably from 0° C. to 50° C., still more preferably from 10° C. to 40° C., and particularly preferably about from 20° C. to 30° C. (room temperature).

(Supply)

The supply refers to the state in which the particulate water absorbing agent is moving into the filling container, and the supply to one filling container may be one time or plural times. Incidentally, the principal force that causes the supply, namely, the movement of the particulate water absorbing agent is preferably gravity. A filling hopper or the like may be vibrated as an auxiliary means, but the auxiliary vibration may cause the fine pulverization of the particulate water absorbing agent, thus it is preferable to conduct the auxiliary vibration only for the discharge of the residue in the filling hopper and the like. Hence, it is preferable that the line for the supply leading to the filling container is set so as to have an angle greater than the angle of repose of the particulate water absorbing agent.

The supply to one filling container may be conducted plural times in order to efficiently fill a predetermined amount of the particulate water absorbing agent. The number of supply is preferably from 2 times to 4 times, more preferably from 2 times to 3 times, and still more preferably 2 times. Examples of a specific embodiment of the supply of plural times may include an embodiment in which the particulate water absorbing agent is supplied by preferably 50% or more of the prescribed amount, more preferably 60% or more, still more preferably 70% or more, particularly preferably 80% or more, and most preferably 90% or more in the first supply and the particulate water absorbing agent is supplied to be in the predetermined amount by the subsequent supply.

It is preferable that the final filling amount (W2) is 100 kg or more, 200 kg or more, 300 kg or more, 400 kg or more, 500 kg or more, 600 kg or more, 700 kg or more, and 800 kg or more in this order on the actual scale (commercial scale). Meanwhile, it is preferable that the final filling amount (W2) is 20000 kg or less, 10000 kg or less, 2000 kg or less, 1500 kg or less, 1200 kg or less, and 1100 kg or less in this order. Hence, According to a preferred embodiment of the filling method of the invention, the W2 is 20000 kg or less in Equation 1-1 above.

In addition, the final filling amount (W2) is preferably less than 100 kg, more preferably 70 kg or less, and still more preferably kg or less on the laboratory scale. Meanwhile, the final filling amount (W2) is preferably 0.5 kg or more, more preferably 1 kg or more, and still more preferably 2 kg or more.

The supply amount per unit time, namely the supply speed is not required be constant in one time of supply and may be different for each supply in plural times of supply. In other words, when conducting the supply plural times, the supply speed may be a constant speed or a non-constant speed, but it is preferable that the supply speed for the second half part (for example, the second time in a case in which the number of supply is two times and the third time in a case in which the number of supply is three times) is the slowest. In this case, the supply speed for the second half part is set to be preferably ⅕ or less and more preferably ⅒ or less the supply speed for the first time. It is preferable to set the supply speed to the above range since the particulate water absorbing agent can be more accurately supplied.

In the invention, the principal force that causes the supply, namely, the movement of the particulate water absorbing agent is preferably gravity, thus the supply speed is greatly dependent on the powder flowability of the particulate water absorbing agent to handle, and as a result, it is preferable to control the "supply time" and the "time from the start of filling to the end of filling" rather than the supply speed. Incidentally, the "supply time" is the total time in the case of conducting the supply of plural times, and the "time from the start of filling to the end of filling" includes the time between the "previous supply" and the "next supply" in the case of conducting the supply of plural times. In other words, there is the time during which the supply is conducted and the time during which the supply is stopped in a case in which the supply is conducted by being divided into plural times, and the "time from the start of filling to the end of filling" is a concept which includes both of them.

The supply time is preferably 5 minutes or shorter, more preferably 4 minutes or shorter, still more preferably 3 minutes or shorter, and particularly preferably 2 minutes or shorter. When the supply time is too short, the packing density (PD) is significantly smaller than the bulk density (BD) so that the particulate waster absorbing agent overflows from the filling container in some cases and from the viewpoint of the control of the predetermined amount, the supply time is preferably 20 seconds or longer, more preferably 30 seconds or longer, still more preferably 50 seconds or longer, and particularly preferably 60 seconds or longer.

In addition, in a case in which the supply is conducted by being divided into plural times, the time from the end of a certain supply to the start of a certain supply, namely, the time during which the supply is discontinued is preferably 5 minutes or shorter, more preferably 4 minutes or shorter, still more preferably 3 minutes or shorter, and particularly preferably 2 minutes or shorter.

(Vibrating Step)

According to a preferred embodiment, the vibrating step is carried out when W1 (particulate water absorbing agent in filling container) is from 10% by weight to 100% by weight based on W2 (final filling amount) where a ratio of the filling amount W1 to the final filling amount W2 of the particulate water absorbing agent is expressed as W1/W2 between the start and the end of the filling step. In other words, the vibrating step is carried out when W1/W2=10% by weight to 100% by weight where the ratio of the filling amount W1 of the particulate water absorbing agent to the final filling amount W2 of the particulate water absorbing agent in the filling container is expressed as W1/W2. Here, it is concerned that the vibrating body moves or deviates from the position in a case in which W1/W2 is less than 10% by weight since a sufficient weight is not applied to the vibrating body.

Moreover, it is possible to obtain a particulate water absorbing agent exhibiting less segregation even "after filling" and "after transport" as the vibrating step which satisfies the following conditions (a) and (b) is carried out at least one time as described above.

(a) The vibration by the vibrating body in contact with the filling container has a vertical directional component and the vibrational angle is within 90'±30° and (b) the total amplitude at no load and a vibration frequency at no load of the vibrating body are set so as to satisfy the following Equation 1-1 and Equation 2 or Equation 1-2 and Equation 2:

1≤acceleration (G)≤13 in a case in which final filling amount of particulate water absorbing agent per filling container: $W2 \geq 100$ kg　　　Equation 1-1

1≤acceleration (G)≤15 in a case in which final filling amount of particulate water absorbing agent per filling container: $W2 < 100$ kg　　　Equation 1-2

27.0≤vibration index≤44.0　　　Equation 2

Incidentally, the acceleration and the vibration index are a value calculated by the following Equation 3 and Equation 4, respectively.

Equation 3

Acceleration (G)=total amplitude at no load (mm)/2/1000×(2π×vibration frequency at no load (Hz))$^3$/9.8　　　Equation 4

Vibration index=42−0.29×vibration frequency at no load (Hz)+1.24×acceleration (G)

Incidentally, the vibration frequency or the total amplitude and the vibrational angle can be measured using the V Checker (type: VC2) manufactured by SINFONIA TECHNOLOGY CO., LTD.

As described above, the filling method of the invention is characterized in that (a) the vibration by the vibrating body in contact with the filling container has a vertical directional component and the vibrational angle is within 90°+30°. In plain words, it is that the vibrational direction of the vibrating body is basically an up-and-down motion in the vertical direction and angled at within ±30° even if it is angled. When the vibrational angle exceeds 30°, that is, the vibration which basically has a horizontal component is conducted, the variation is not caused in the filled particulate water absorbing agent at the stage of (I) above, namely, immediately after filling, but the segregation is caused in the filled particulate water absorbing agent at the stage of (III) above when the filled particulate water absorbing agent is transported at the stage of (II) above.

The vibrating body refers to the site including both 12; a vibration generator and 10; a mounting portion in FIG. 1. Incidentally, it is preferable that these sites are integrated.

In addition, setting of the condition for the vibration filling in the invention (namely, vibration condition in which the acceleration and vibration index of the invention are calculated) is conducted in a state in which 26; a pallet and 16; the filling container are not mounted on the vibrating body, namely, a no load state.

In addition, the pallet is more preferably a replaceable plate-like body on which the filling container can be mounted. Incidentally, the entire surface of the plate-like body is not required to be flat (plane), but it may be a drainboard-like or lattice-like plate, and further it may be a mesh-like plate or a perforated plate. The plate-like body is preferably has a mass of from 5 kg to 50 kg per 1 t of the mass of W2 and more preferably has a hollow structure. The plate-like body can have a sufficient strength and the handling property thereof is also improved as the mass is from 5 kg to 50 kg. In addition, as the plate-like body has a hollow structure, not only it is easy to move the filling container after filling using a forklift or the like but also an effect of further promoting the effect of the invention can be obtained. The reason for the latter is not clear, but it is believed that it is suppressed that the vibration generated by the vibration generator is attenuated by the mass of the particulate water absorbing agent. Hence, According to a preferred embodiment of the filling method of the invention, the pallet is a replaceable plate-like body having a mass of from 5 kg to 50 kg per 1 t of the particulate water absorbing agent. In other words, it is that the pallet is preferably a replaceable plate-like body having a mass of from 5 kg to 50 kg in the case of expecting 1 t as the final filling amount W2. Incidentally, in the present specification, the term "replaceable" means that the pallet itself may be replaceable or a part of the pallet may be replaceable by repairing or the like when the part of the pallet is broken or the like.

Examples of the material for the pallet may include wood, a plastic, a metal, paper, and the like, and wood or a plastic is preferable. Incidentally, it is not required to be made of wood or a plastic only, but parts such as nails or installing brackets may be joined thereto.

In the case of wood, the weight per one sheet is preferably from kg to 50 kg and more preferably from 10 kg to 30 kg. In addition, the weight per area of the upper surface (for example, 12,100 cm$^3$ in a case in which the length is 110 cm and the width is 110 cm, the gap between the plates is also included in the area) is preferably from 0.4 (g/cm$^2$) to 4.1 (g/cm$^2$) and more preferably from 0.8 (g/cm$^2$) to 2.5 (g/cm$^2$). A technical effect is obtained that the effect of the invention is easily obtained as the vibration is efficiently transmitted when the weight is in such a range.

In the case of a plastic, the weight per one sheet is preferably from 5 kg to 50 kg and more preferably from 10 kg to 25 kg. In addition, the weight per area of the upper surface (for example, 12,100 cm$^2$ in a case in which the length is 110 cm and the width is 110 cm, the gap between the plates is also included in the area) is preferably from 0.4 (g/cm$^2$) to 4.1 (g/cm$^2$) and more preferably from 0.8 (g/cm$^2$) to 2.1 (g/cm$^2$). A technical effect is obtained that the effect of the invention is easily obtained as the vibration is efficiently transmitted when the weight is in such a range.

As described above, in the filling method of the invention, the effect of the invention is not obtained when the vibration by the vibrating body is generated only in the horizontal direction, by only the so-called rolling, but the vibration in the vertical direction is required. In addition, it is impossible to obtain the effect of the invention when the vibrational angle exceeds 30° even if the vibration has a vibrational component in the vertical direction. As described above, in the filling method of the invention, the vibration is not required to be only the complete vertical vibration, but the vibrational angle is required to be within ±30° from the vertical direction (90°).

Incidentally, in the present specification, the term "vibrational angle" is the angle of the vibrational direction axis formed by the vertical direction axis and the horizontal axis that is obtained by the projection of the vertical direction axis onto the horizontal plane.

Incidentally, the vibrational direction axis is the vibrational direction in a case in which the vibration by the vibrating body is the linear vibration, and it is the maximum amplitude direction in a case in which the vibration by the vibrating body is the non-linear vibration. Such a vibrational angle is preferably within 90°+20°, more preferably within 90°±10°, and still more preferably within 90°±5°.

In addition, it is regarded as the non-linear vibration (in particular, elliptical vibration) in a case in which there is the minor axis amplitude to be 10% or more of the major axis amplitude. In a case in which the vibration by the vibrating body is the non-linear vibration, the ratio of the minor axis amplitude that is the maximum amplitude in the vertical direction with respect to the amplitude direction axis to the major axis amplitude that is the total amplitude of the vibrational direction axis is preferably more than 0% and 60%, more preferably 50% or less, still more preferably 30% or less, and particularly preferably 10% or less. It is possible to suppress the vibration in the horizontal direction when the ratio is in such a range.

Furthermore, it is preferable that the total amplitude of the vibrating body at no load is 0.25 m or more, 0.3 mm or more, 0.5 mm or more, and 1.0 mm or more in this order. In particular, it is possible to efficiently exhibit the effect of the invention when the total amplitude is 0.3 m or more. From the viewpoint of suppressing an excessive burden on the vibrating body, the amplitude V1 is preferably 50 mm or less, more preferably 10 mm or less, still more preferably 6 mm or less, and particularly preferably 5 mm or less. Incidentally, the term "amplitude" and the term "total amplitude" are handled to be synonymous with each other in the present specification.

In addition, it is preferable that the vibration frequency of the vibrating body at no load is from 10 Hz to 90 Hz. It is difficult to obtain the effect of the invention when the vibration frequency is less than 10 Hz, and the effect of the invention diminishes in the same manner when the vibration frequency is more than 90 Hz. The vibration frequency is more preferably from 15 Hz to 80 Hz, still more preferably from 20 Hz to 75 Hz, and particularly preferably from 20 Hz to 70 Hz. Incidentally, there is also a case in which the "vibration frequency" is written as the "frequency".

In the vibrating method of the invention, in a case in which the final filling amount of the particulate water absorbing agent: $W2 \geq 100$ kg, it satisfies $1 \leq$ acceleration $(G) \leq 13$, but the acceleration is preferably 10 G or less, more preferably from 1.5 G to 9.5 G, still more preferably from 1.6 G to 9.0 G, and particularly preferably from 1.8 G to 8.5 G. In such an embodiment, the effect of the invention is not obtained in a case in which the acceleration is less than 1 G since the vibration is not sufficient, and it is concerned that the apparatus is damaged in a case in which the acceleration is more than 13 G. In addition, it is concerned that the segregation cannot be suppressed. On the other hand, not only the damage of the filling apparatus is prevented but also a technical effect that the effect of the invention is remarkably exhibited is obtained particularly in a case in which the acceleration is 10 G less.

In addition, in the vibrating method of the invention, in a case in which the final filling amount of the particulate water absorbing agent: $W2 < 100$ kg, it satisfies $1 \leq$ acceleration $\leq 15$, but the acceleration in such an embodiment is preferably from 1.0 G to 15 G, more preferably from 1.5 G to 14.8 G, and still more preferably from 1.8 G to 14.6 G. The present embodiment defines a laboratory scale in particular. In a case in which the weight of the particulate water absorbing agent to be filled is significantly light (namely, a case in which the final filling amount of the particulate water absorbing agent: $W2 < 100$ kg), the risk of breakage and the like is low and also the filling can be conducted while suppressing the segregation even though the acceleration exceeds 13 G. However, the segregation occurs and the effect of the invention cannot be obtained when the acceleration exceeds 15 G.

Here, the vibration index is an index which indicates that the effect of the invention is exerted in a case in which the acceleration and the vibration frequency are in a specific relation. In other words, the "vibration index" is one obtained through the indexation of the volume reduction effect (amount of change in bulk specific gravity of powder) when conducting the vibration filling while changing the amplitude and the acceleration, and it means a value calculated from a mathematical formula that is derived by performing a multiple regression analysis by adopting the volume reduction effect as the objective variable and the numerical values of the amplitude and the acceleration as the explanatory variable. The vibration index correlates with the segregation preventing effect of the invention, and the effect of the invention is remarkably obtained by having a specific vibration index. More specific deriving method is described in the section of Examples.

The vibration index is preferably from 27.0 to 44.0, more preferably from 28.0 to 43.8, and still more preferably from 30.0 to 43.6. It is concerned that the vibration is not sufficient in a case in which the vibration index is less than 27.0, and it is concerned that the apparatus is damaged in a case in which the vibration index is more than 44.0.

Furthermore, it is also preferable that the supply is conducted plural times and at least one time of vibrating step is carried out between the stop of the supply and the start of the next supply.

It is more preferable that the vibrating step is carried out when the amount W1 of the particulate water absorbing agent in the filling container to the final filling amount W2, namely, W1/W2 is from 30% by weight to 100% by weight.

Furthermore, W1/W2 is still more preferably from 40% by weight to 95% by weight in a case in which the number of supply is two times. In addition, according to another embodiment of the invention, the particulate water absorbing agent goes through the state of being subjected to the vibrating step only at the time point at which W1/W2 is any of from 30% by weight to 95% by weight.

Incidentally, it is not preferable that the time for the vibrating step is too short since it is concerned that the effect of the invention is not sufficiently obtained, and it is not preferable that the time is too long since it is concerned that the crushing of the particulate water absorbing agent occurs. Hence, the vibration time is preferably from 10 seconds to 60 seconds, more preferably from 15 seconds to 45 seconds, and still more preferably from 20 seconds to 40 seconds.

In addition, the particulate water absorbing agent is accumulated in the filling container by supplying the particulate water absorbing agent into the filling container in the filling step. The particulate water absorbing agent is deposited by continuing the supply while carrying out the vibrating step depending on the case. According to a preferred embodiment of the filling method of the invention, the relative humidity in the space portion within 30 cm from the surface of the deposited particulate water absorbing agent is from 30% RH to 65% RH. By having such an embodiment, a technical effect that the aggregation of the particles does not occur and the effect of the invention is easily obtained is exhibited. In the invention, the physical properties of the particulate water absorbing agent can be enhanced due to the suppression of moisture absorption and the like.

(Filling and Vibrating Apparatus)

The machine (vibrating apparatus) of the invention is suitable for filling of the particulate water absorbing agent that is continuously produced on a production scale (upper limit of about 15 (t/h)) of preferably 500 (kg/h) or more, more preferably 1 (t/h) or more, and still more preferably 1.5 (t/h).

In addition, according to the invention, a machine that is equipped with the filling and vibration functions and used in the filling method of the invention is provided as well.

The filling apparatus 2 illustrated in FIG. 1 includes a hopper 4, an intermediate portion 6 equipped with a thermostat, a discharge control unit 8 equipped with a butterfly damper, the discharge port 18, the mounting portion 10, the vibration generator 12, and a frame 14.

The form illustrated in FIG. 1 is an example in which a flexible container bag illustrated by a two-dot chain line is used as the filling container 16, and thus a hanging belt 20 joined to the flexible container bag, a hanging portion 22 on which the hanging belt 20 is hooked, and a pallet 26 are illustrated.

Incidentally, the flexible container bag of the filling container 16 is fixed by attaching the opening thereof to the discharge port 18 and hooking the hanging belt 20 on the hanging portion 22.

The particulate water absorbing agent that has been supplied to the hopper 4 is supplied from the discharge port 18 into the filling container 16 through the intermediate portion 6 and the discharge control unit 8. The adjustment of the supply amount of the particulate water absorbing agent can be conducted by a method in which the particulate water absorbing agent is supplied to the hopper 4 after being weighed in advance, a method to conduct the adjustment using a metering hopper equipped with a metering function as the hopper 4, a method to conduct the adjustment using a balance installed under the vibration generator 12, and the like, and plural methods can also be combined.

It is more preferable that the hopper 4 and/or the intermediate portion 6 are equipped with a heat retaining mechanism and/or a temperature control mechanism.

The discharge control unit 8 is a site which controls the start and stop of the supply. In a case in which the supply amount of the particulate water absorbing agent is adjusted using the balance installed under the vibration generator 12, a flow rate adjuster (not illustrated) may be equipped to the upstream or downstream of the discharge control unit 8 or it is preferable that the discharge control unit 8 itself is equipped with such a function since it is possible to increase the precision of weighing.

The mounting portion 10 may be concurrently used as the vibrating body by directly mounting the filling container 16 thereon or may have a structure to mount the pallet 26 thereon. It is preferable that an upper surface 24 of the mounting portion 10 is horizontal or has a shape which allows the upper surface of the pallet 26 to be horizontal. The shape is preferable since the bottom of the filling container 16 becomes horizontal by the shape and thus the vibration is uniformly applied to the particulate water absorbing agent in the filling container.

The vibration generator 12 is the source of vibration. The vibration generator 12 can be selected from various kinds of types such as an unbalanced mass type, an oil hydraulic type, and an electro-dynamic type. It is difficult to increase the total amplitude in the case of an electro-dynamic type, it takes time and effort for the maintenance in the case of a hydraulic type, and a non-linear vibration is generated in the case of an unbalanced mass type although it is inexpensive and the maintenance thereof is easy. Hence, an embodiment is more preferable that a plurality of unbalanced mass-type vibration generators is disposed so as to cancel the amplitude in the horizontal direction and the vibration period is adjusted. By having such a configuration, it is possible to significantly decrease the vibration in the horizontal direction, it is possible to decrease the segregation of the filled particulate water absorbing agent, and it is possible to exhibit the effect of the invention.

In other words, in a preferred embodiment of the filling method of the invention, a plurality of unbalanced mass-type vibration generators are used for the generation of the vibration, the vibration generators are disposed so as to cancel the amplitude in the horizontal direction, whereby the vibrational direction is adjusted.

The unbalanced mass type is a so-called vibration motor, and it is possible to use a known vibration motor. Examples of the vibration motor may include KEE Series such as "KEE-16-2, (hereinafter, KEE- is abbreviated) 23-2, 30-2, 40-2, 17-4, 24-4, 34-4, 52-4B, 75-48, 84-4C, 110-4, 24-6C, 34-6, 45-6B, 60-6B, 80-6C, 110-6, 140-6, 165-6, 185-6, 32-8, 35-8R, 54-8B, 60-8BR, 85-8, 100-8R, 110-8B, 125-8R, 135-8B, 150-8R, 170-8B, and 185-8BR" manufactured by URAS TECHNO CO., LTD., KM-2PA such as "KM170-2PA" of a trade name and KM-4PA series manufactured by EXEN Corp., NEG/NEA series such as "NEG/NEAS0550" manufactured by NetterVibration, and the like. In addition, it is also possible to apply the excitation apparatus exemplified in JP 10-034084 A other than the vibration motor.

It is preferable that the filling container 16 is installed such that the contact thereof with things other than the pallet 26 (the mounting portion 10 in a case in which the pallet 26 is not used) is minimized. A method to use a member or to have a structure which does not attenuate the vibration of the filling container 16 is preferable in a case in which the filling container 16 is brought into contact with things other than the pallet 26 for fixation and the like.

For example, it is preferable that the hanging belt 20 uses a soft material such as cloth and has a structure to allow play at the contact portion with the filling container 16, a structure to allow play at the contact portion with the hanging portion 22, and the like. In addition, it is preferable that the hanging portion 22 uses a soft material such as cloth and has a structure to allow play at the contact portion with the frame or the like, and the like. In addition, it is preferable to employ a mode in which the filling container 16 is not fixed to the discharge port 18 or to use a flexible hose for the connection in a case in which the filling container 16 is constituted by a hard material such as a drum can. It is possible to smoothly conduct the filling by having such an embodiment.

It is more preferable that the pallet 26 is a so-called pallet of a plate-like body having a hollow structure and a structure in which the fork of a forklift can be inserted into the plate-like body since the movement of the filling container 16 after filling is easier as well as the effect of the invention can be sufficiently obtained.

The filling method of the invention can be efficiently carried out while appropriately considering various conditions (for example, the weight of the filled product, the supply speed, and the temperature and humidity of the environment) as described above.

The particulate water absorbing agent filled in accordance with the filling method of the invention goes through the stage of (I) (namely, after filling) above and the stage of (II) (namely, transport) above, whereby it is possible to decrease (that is, it is possible to decrease the bias of the fine powder among the respective lots) the deflection of the content of the particulate water absorbing agent which passes through a 150 μm mesh (namely, the proportion of the particles having a size of less than 150 μm) among the respective lots in the stage of (III) (namely, the absorbent article) above.

In addition, according to the filling method of the invention, the particulate water absorbing agent that is subdivided from the filled particulate water absorbing agent maintains a high SPC, and the deflection thereof can be suppressed. The absorbent article such as a diaper using such a particulate water absorbing agent favorably absorbs the body fluids and the like.

<Method for Sampling Filled Particulate Water Absorbing Agent>

Subsequently, the method for sampling the filled particulate water absorbing agent of the invention (in the present specification, also simply referred to as the "sampling method of the invention") will be described.

The sampling method of the invention is a method for sampling the filled particulate water absorbing agent that is filled in the filling container and has a filling volume of V ($cm^3$), and the sampling number n (times) and the distance x (cm) among the respective sampling points adjacent to one another are set such that the following conditions (1) and (2) are necessarily satisfied.

[Mathematical Formula 9]

$$n \geq m \qquad (1)$$

with the proviso that, m is greater one of 3 and $$\lfloor V/100000 \rfloor \qquad \text{[Mathematical Formula 10]}$$

[Mathematical Formula 11]

$$x \geq y \qquad (2)$$

with the proviso that, $$y = \frac{\sqrt[3]{V}}{\left[\sqrt[3]{m}\right] + 1} \qquad \text{[Mathematical Formula 12]}$$

Sampling is an operation that is commonly practiced in the research and development, but sampling is difficult in the case of one, such as a particulate water absorbing agent, which has a shape that is not a true sphere but a constant particle size distribution. Meanwhile, those who provide a particulate water absorbing agent and those who manufacture an absorbent article using the particulate water absorbing agent are both required to sample the particulate water absorbing agent with high precision to know the specifications of the respective water absorption physical properties.

According to the method of the invention, it is possible to provide a highly precise sampling method for the filled particulate water absorbing agent. For this reason, a highly reliable method for determining the specifications of the filled particulate water absorbing agent is provided by setting the arithmetic mean values of the water absorption physical property values obtained by analyzing the respective samples sampled by the method of the invention as the representative water absorption physical property values of the filled particulate water absorbing agent, namely, by that. Hence, in the invention, a method for determining the representative water absorption physical property values of the filled particulate water absorbing agent utilizing the sampling method of the invention is also provided.

Accordingly, it is possible to provide a highly precise sampling method of the filled particulate water absorbing agent (a method for determining the representative water absorption physical property values of the filled particulate water absorbing agent) by having a configuration as described above, and thus it is possible to provide a technique in which a decrease in physical properties is suppressed or consumer complaints are diminished.

In the invention, in the case of sampling the filled particulate water absorbing agent, it is possible to realize a highly precise sampling by setting n (times) and x (cm) where n (times) denotes the sampling number and x (cm) denotes the distance among the respective sampling points adjacent to one another such that a specific condition is necessarily satisfied. Hereinafter, the sampling method will be described in detail.

The specific condition is as follows.

[Mathematical Formula 13]

$$n \geq m \qquad (1)$$

with the proviso that, m is greater one of 3 and $$\lfloor V/100000 \rfloor \qquad \text{[Mathematical Formula 14]}$$

[Mathematical Formula 15]

$$x \geq y \qquad (2)$$

with the proviso that,
It is $$y = \frac{\sqrt[3]{V}}{\left[\sqrt[3]{m}\right] + 1} \qquad \text{[Mathematical Formula 16]}$$

It is possible to realize a highly precise sampling by setting the sampling number n (times) and the distance x (cm) among the respective sampling points adjacent to one another such that the above conditions (1) and (2) are necessarily satisfied in this manner.

(1) Number of Sampling Points

In the invention, when the sampling number is denoted as n (times),

[Mathematical Formula 17]

$$n \geq m \qquad (1)$$

with the proviso that, m is greater one of 3 and $$\lfloor V/100000 \rfloor \qquad \text{[Mathematical Formula 18]}$$

In plain words, it is essential that the sampling number (n times) is 3 or more regardless of the size of the filling volume V ($cm^3$). It is impossible to conduct highly reliable sampling when n<3 (namely, 2 or less).

In addition, in a case in which the filling volume V ($cm^3$) is increased and
The result of $$\lfloor V/100000 \rfloor \qquad \text{[Mathematical Formula 19]}$$

is 4 or more, the lower limit value of the sampling number (n times) is determined based on the value calculated by the Equation.

Incidentally, the Equation is a floor function, that is, the largest integer that is equal to or less than the real number with respect to a certain real number.

(1) above will be described with reference to a specific example. In a case in which the shape of the filling container is cylindrical, the particulate water absorbing agent is filled in the filling container, the height of the filled particulate water absorbing agent is 145 cm, and the diameter of the cross section of the horizontal plane is 110 cm, it is v=55× 55×3.14×145=1377282.5 ($cm^3$). Hence, it is 1,377,282.5/ 100,000=13.77, and as a result, it is 13. It is m=13 since 13 is 3 or more.

In other words, in the case of the above specific example, the sampling number (n times) should be 13 or more. In this case, it is impossible to conduct highly reliable sampling when it is n<13 (namely, 12 or less).

(2) Distance Between Sampling Center Points

In the invention, when the distance among the respective sampling points adjacent to one another is denoted as x (cm),

[Mathematical Formula 20]

$$x \geq y \qquad (2)$$

with the proviso that, it is $$y = \frac{\sqrt[3]{V}}{\left[\sqrt[3]{m}\right]+1} \qquad \text{[Mathematical Formula 21]}$$

Here, the "distance among the respective sampling points adjacent to one another" is measured as the distance between the "center points" of the respective sampling points. Hence, in plain words, the "distance among the respective sampling points adjacent to one another" is also said as the "distance among the sampling center points".

Here, it is defined in the denominator of the Equation.

$$\left[\sqrt[3]{m}\right] \qquad \text{[Mathematical Formula 22]}$$

It is a ceiling function, that is, it is the smallest integer that is equal to or greater than the real number with respect to a certain real number.

Hence, when it is applied to the above specific example, first, the numerator is the cube root of 1377282.5 to be "111.26". In addition, in the denominator, $$\left[\sqrt[3]{13}\right] \qquad \text{[Mathematical Formula 23]}$$

it is "3", as a result, it is y=111.26/(3+1)=27.8.

In other words, it is that the distance x (cm) among the respective sampling points adjacent to one another should be secured to be at least 27.8 cm. This should be satisfied in all the distances determined by arbitrary two sampling points.

It is biased sampling in the case of conducting sampling at intervals narrower than 27.8 cm even if the sampling is conducted at 13 points, and thus it can be said that the sampling is lacking in reliability to determine the representative physical property values.

In the invention, the "three-dimensional (filled particulate water absorbing agent)" having any shape can also be considered in terms of a "straight line" by adopting the concept of "cube root" in this manner. The minimum value of the sampling number is determined depending on the volume, but it is possible to conduct "equal" sampling in accordance with the sampling number when conducting the sampling on the basis of the minimum value of the sampling number, and thus it is possible to significantly decrease the variation.

By satisfying the condition of (2) above in this manner, the sampling does not become random sampling, and thus it is possible to determine highly reliable representative physical property values of the filled particulate water absorbing agent. Incidentally, the reason why "1" is added to the denominator is because the "straight line" is divided by the "point" (the idea of the so-called tree-planting problem).

Incidentally, the collection amount (a) per one sampling point is not particularly limited as long as it is the amount required for the analysis of physical properties of the particulate water absorbing agent. Here, the amount required for the analysis of physical properties is, for example, the amount required to measure the physical properties such as CRC, SFC, AAP, and FSR. This amount is obtained in Examples of this application or by the use of common sense in the art. However, it is preferable to set the upper limit so as to satisfy the following:

$$n \times s < V \times 10^6 \times 0.05 \qquad \text{[Mathematical Formula 24]}$$

Such a sampling amount is a realistic amount from the viewpoint of "sampling".

In addition, the sampling instrument (sampler) for sampling is also not particularly limited. The sampling instrument may be a pipe to which a sampling window is attached or a pipe to which a sampling window is not attached. In the case of the former, it is possible to sample the filled particulate water absorbing agent by piercing the filled particulate water absorbing agent with the pipe, taking the particulate water absorbing agent into the sampling window, and pulling it out. In addition, in the case of the latter, it is possible to take the particulate water absorbing agent in the inside of the filling container by piercing the side of the filling container with the pipe and inclining the filling container. Incidentally, in the case of the former, the pipe may be one to which plural sampling windows are attached. In addition, in the case of the latter, it is required to close the through hole with adhesive tape or the like after sampling.

As described above, according to the sampling method of the invention, it is possible to provide a highly precise sampling technique, and it is possible to suppress a decrease in physical properties depending on the lot and to diminish the consumer complaints.

<Filled Particulate Water Absorbing Agent>

Subsequently, the filled particulate water absorbing agent of the invention will be described.

In the present specification, the filled particulate water absorbing agent means the particulate water absorbing agent filled in the filling container.

A preferred embodiment of the filled particulate water absorbing agent of the invention is a filled particulate water absorbing agent in which the relative standard deviations of the respective physical property values of the particulate water absorbing agents sampled from the same filled particulate water absorbing agent at three or more points satisfy at least one of the following (a) to (d):

(a) the relative standard deviation of the centrifuge retention capacity (CRC) is 2% or less;

(b) the relative standard deviation of the saline flow conductivity (SPC) is 6% or less;

(c) the relative standard deviation of the absorbency against pressure (AAP) is 1% or less; and (d) the relative standard deviation of the free swell rate (FSR) is 5% or less.

According to a preferred embodiment, a filled particulate water absorbing agent which satisfies at least (a) and (b) or (a) and (c) is preferable, and a filled particulate water absorbing agent which satisfies at least (a) to (c) is more preferable, and a filled particulate water absorbing agent which satisfies all of (a) to (d) is still more preferable.

In addition, according to another embodiment of the invention, a filled particulate water absorbing agent that is filled by the filling method of the invention is provided. According to such embodiment, the segregation of the filled particulate water absorbing agent is significantly suppressed and particularly the filled particulate water absorbing agent satisfies at least one of (a) to (d).

As described above, it has been found that there is a problem in practice that the water absorption physical property values of the respective final products (absorbent articles) after the final products (absorbent articles) which contain the particulate water absorbing agent at from several to several tens of g as one unit is completed at the stage of (III) above deviate from the specifications provided at the stage of (I) above in some cases.

The present inventors have focused on the stage of (II) above in the course of intensive studies on the factor thereof. In other words, in the stage of (I) above, the particulate water absorbing agent is filled in the filling container by from several hundreds to several thousands of kg as one unit and thus this filling container is usually transported by a means of transport such as a truck. The present inventors have focused on the "jolting" during this transport. In other words, it has been found out that segregation can be caused by the "jolting" during transport even in a case in which a less segregated state is achieved at the stage of (I) above. In the invention, it is possible to provide a filled particulate water absorbing agent exhibiting significantly less segregation not only at the stage of (I) above but also at the stage of (III) above by densely packing the filled particulate water absorbing agent at the stage of (I) above in anticipation of the "jolting" during transport, and thus it is possible to significantly decrease the variation in water absorption physical property values of the respective final products (absorbent articles). Incidentally, the term "from several hundreds to several thousands of kg" refers to about from 100 kg to 100,000 kg or from 500 kg to 50,000 kg as a guideline.

In the filled particulate water absorbing agent filled in accordance with the filling method of the invention and the filled particulate water absorbing agent after transport, the deflection of the content of the particulate water absorbing agent which passes through a 150 μm mesh (namely, the proportion of the particles having a size of less than 150 μm) decreases in the respective particulate water absorbing agents subdivided therefrom. For this reason, it is possible to suppress the deflection of AAP or SFC that is easily affected by the presence of the particles having a size of less than 150 μm in the particulate water absorbing agent subdivided from the filled particulate water absorbing agent filled in accordance with the filling method of the invention.

In consideration of the suppressing effect of the deflection of AAP, SPC or the like, the logarithmic standard deviation ($\sigma\xi$) of the particle size distribution of the particulate water absorbing agent which passes through a 150 μm mesh (namely, the proportion (% by weight) of the particles having a size of less than 150 μm) in the particulate water absorbing agent subdivided from the filled particulate water absorbing agent filled by the filling method of the invention is preferably 0.1 or more and less than 0.29, more preferably from 0.12 to 0.28, and still more preferably from 0.15 to 0.25.

Incidentally, according to a preferred embodiment, (a) the relative standard deviation of the centrifuge retention capacity (CRC) is preferably from 0% to 1.6% and more preferably from 0% to 1.3%.

In addition, according to a preferred from, (b) the relative standard deviation of the saline flow conductivity (SPC) is preferably from 0% to 5.6% and more preferably from 0% to 5.5%. It is possible to stably maintain the SFC of the particulate water absorbent resin as a final product at a high level when the saline flow conductivity has such a value. However, the saline flow conductivity is 4.0% or more and 4.5% or more in some cases.

In addition, according to a preferred from, (c) the relative standard deviation of the absorbency against pressure (AAP) is preferably from 0% to 0.9%.

In addition, according to a preferred from, the relative standard deviation of the free swell rate (PSR) is preferably from 0% to 4.8% and more preferably from 0% to 4.6%.

A preferred embodiment for having such a relative standard deviation is not particularly limited, but it is preferably a method in which the filled particulate water absorbing agent is fabricated using the filling method of the invention.

Here, the method for sampling the filled particulate water absorbing agent described above may be or may not be the sampling method of the invention. In the case of fabricating the filled particulate water absorbing agent using the filling method of the invention, it is possible not only to achieve a state in which segregation does not occur in the particle size distribution at the stage of (I) above but also to achieve a less segregated state even after the filled particulate water absorbing agent is transported by a means of transport such as a truck in (II) above and to maintain a less segregated state even at the time point at which uniform final products are fabricated in (III) above. In other words, the segregation of the filled particulate water absorbing agent is low at any time point, and thus highly precise sampling is conducted even without using the sampling method of the invention since the segregation of the target material to be sampled (filled particulate water absorbing agent) is already low.

Accordingly, it can be said that the sampling method in the method of the invention easily exerts its effect when the segregation of the target material (filled particulate water absorbing agent) to be sampled is high and the representative water absorption physical property values having higher reliability can be determined. However, the invention which provides the method for determining the representative water absorption physical property values having higher reliability has the effect of diminishing the consumer complaints.

It is as described above that the present inventors have completed the filling method of the invention by finding out that it is possible to suppress the segregation of the water absorbent resin particles (particularly water absorbent resin particles having a high water absorbent speed) not only at the time of filling but also during transport by controlling the vibration force applied at the time of filling.

Hereinafter, the respective water absorption physical property values of the filled particulate water absorbing agent will be described.

[AAP](ERT 442.2-02)

The absorbency against pressure (AAP) with respect to saline at a load of 4.8 kPa that is defined in ERT 442.2-02 and one of the representative water absorption physical property values of the particulate water absorbing agents sampled at three or more points is preferably 15 (g/g) or more. An absorbent article such as a diaper using such a particulate water absorbing agent favorably absorbs the body fluids and the like. The AAP of the particulate water absorbing agent is more preferably 20 (g/g) or more, still more preferably 22 (g/g) or more, further still more preferably 23.5 (g/g) or more, particularly preferably 24 (g/g) or more, and most preferably 26 (g/g) or more. Meanwhile, the upper limit of the absorbency against pressure is not particularly limited since the absorbent article has higher physical properties as the absorbency against pressure is higher, but it is believed that the upper limit of this absorbency against pressure is about 35 (g/g) from the viewpoint of being difficult to produce and a steep rise in cost. Incidentally, this absorbency against pressure with respect to saline at a load of 4.8 kPa is also referred to as the AAP (4.8 kPa) or simply the AAP in this application.

The standard deviation of the AAP of the particulate water absorbing agent after being filled by the method of the invention is preferably from 0.01 to 0.30 and more preferably from 0.15 to 0.25. It is possible to maintain the AAP of the particulate water absorbent resin of a final product at a high level when the standard deviation is in such a range.

In addition, by filling the particulate water absorbing agent by the filling method of the invention, the deflection among the respective lots of the absorbent article to be produced using the particulate water absorbing agent that is subdivided from the filling container or among the respective articles is reduced and it is possible to stably produce an absorbent article which is required particularly to have a stable AAP or SFC, CRC, and FSR to be described below of the particulate water absorbing agent.

(SPC)

It is preferable that the saline flow conductivity (SFC) that is one of the representative water absorption physical property values of the particulate water absorbing agents sampled at three or more points is 20 ($\times 10^{-7} \cdot cm^3 \cdot s \cdot g^{-1}$) or more, 30 ($\times 10^{-7} \cdot cm^3 \cdot s \cdot g^{-1}$) or more, 35 ($\times 10^{-7} \cdot cm^3 \cdot s \cdot g^{-1}$) or more, 40 ($\times 10^{-7} \cdot cm^3 \cdot s \cdot g^{-1}$) or more, 45 ($\times 10^{-7} \cdot cm^3 \cdot s \cdot g^{-1}$) or more, and 45.5 ($\times 10^{-7} \cdot cm^3 \cdot s \cdot g^{-1}$) or more in this order. However, in reality, the saline flow conductivity is about 1000 ($\times 10^{-7} \cdot cm^2 \cdot s \cdot g^{-1}$) or less in consideration of the CRC to be described later. An absorbent article such as a diaper using such a particulate water absorbing agent favorably absorbs the body fluids and the like.

According to the filling method of the invention, the filled particulate water absorbing agent after filling maintains a high SFC, and the deflection thereof can be suppressed. An absorbent article such as a diaper using such a particulate water absorbing agent favorably absorbs the body fluids and the like. In addition, in a case in which such a particulate water absorbing agent is contained in an absorbent article, the absorbent speed of urine is properly maintained and the occurrence of leakage is also suppressed even in a case in which the concentration of the particulate water absorbing agent contained in the article is 30% by weight or more and more specifically 50% by weight or more.

[CRC]

The centrifuge retention capacity (CRC) of the particulate water absorbing agent with respect to saline that is one of the representative water absorption physical property values of the particulate water absorbing agents sampled at three or more points is preferably 5 (g/g) or more, more preferably 15 (g/g) or more, and still more preferably (g/g) or more. The upper limit of the centrifuge retention capacity is not particularly limited, but it is about 60 (g/g), 45 (g/g), or 40 (g/g) in reality.

[FSR]

The free swell rate (FSR) that is one of the representative water absorption physical property values of the particulate water absorbing agents sampled at three or more points is preferably 0.20 (g/g/s) or more, more preferably at 0.24 (g/g/s) or more, still more preferably 0.25 (g/g/s) or more, and particularly preferably 0.30 (g/g/s) or more. The upper limit of this FSR is not particularly limited, but it is about 1.00 (g/g/a), 0.50 (g/g/s), or 0.45 (g/g/s) in reality.

Incidentally, such numerical values can be obtained not only at (I) above but also at the stage of the (III) above when the filling is conducted by the filling method of the invention. There is generally a tendency that the segregation is easily caused during transport of the stage of (II) above particularly in a particulate water absorbing agent which has a fast water absorbent speed to be in the above range (particularly FSR is 0.25 or more) at the time point of (I) above since the bulk specific gravity is low, but according to the filling method of the invention, the segregation suppressing effect during transport is remarkably exhibited, and thus it is possible to provide a particulate water absorbing agent exhibiting less segregation even at the stage of (III) above.

Accordingly, a third preferred embodiment of the invention is a filled particulate water absorbing agent in which the arithmetic mean values of the representative water absorption physical property values of the particulate water absorbing agents sampled at three or more points satisfy at least one of the following (e) to (h):

(e) CRC is from 5 to 40 (g/g);
(f) SFC is 20 ($\times 10^{-7} \cdot cm^3 \cdot s \cdot g^{-1}$) or more;
(g) AAP is 20 (g/g) or more; and
(h) FSR is 0.25 (g/g/s) or more.

Incidentally, the sampling method with regard to the phrase "sampled at three or more points" described in the present specification may be or may not be the sampling method of the invention. In addition, it is desired that the arithmetic mean values satisfy at least two or more, preferably 3 or more, and more preferably all of four of (e) to (h) above.

However, in the filled particulate water absorbing agent filled by the filling method of the invention, it is possible not only to achieve a state in which segregation does not occur in the particle size distribution at the stage of (I) above, but also to achieve a less segregated state even after the filled particulate water absorbing agent is transported by a means of transport such as a truck in (II) above and to maintain a less segregated state even at the time point at which uniform final products are fabricated in (III) above. In other words, the segregation of the filled particulate water absorbing agent is low at any time point, and consequently highly precise sampling is conducted even without using the sampling method of the invention.

(Bulk Specific Gravity)

In addition, according to a preferred embodiment, the bulk specific gravity of the particulate water absorbing agent in the filled particulate water absorbing agent of the invention is usually from 0.45 (g/ml) to 0.75 (g/ml), preferably from 0.50 (g/ml) to 0.70 (g/ml), and more preferably from 0.55 (g/ml) to 0.65 (g/ml). It is preferable that the bulk specific gravity is 0.50 (g/ml) or more from the viewpoint of being able to produce a particulate water absorbing agent having a high absorbent speed. It is suitable that the bulk specific gravity is 0.70 (g/ml) or less from the viewpoint of obtaining a desired absorbent speed.

<Storage and Transport>

According to the invention, a storage method or a transport method of the filled particulate water absorbing agent of the invention is provided.

In particular, the particulate water absorbing agent filled in a filling container by the filling method of the invention is suitable for long term storage and long-distance transport since the segregation of the filled particulate water absorbing agent "after filling" is hardly caused.

The storage time is appropriately determined in from 1 day to 100 days and further from 10 days to 100 days. The means of transport may be any of a truck, a train, a container ship, or the like, and the transport distance is appropriately determined in a range of from 1 km to 100000 km or from 10 km to 10000 km. The transport time is appropriately determined in from 1 hour to 100 days and further from hours to 100 days.

The storage and the transport may be either one or both of them, it is preferable to transport after storage, and the filled particulate water absorbing agent may be further stored.

<Absorbent Article>

According to the invention, absorbent articles, particularly paper diapers, sanitary napkins, and napkins for incontinents which contain the particulate water absorbing agent that is subdivided from the filled particulate water absorbing agent of the invention into preferably from 0.1 g to 100 g, more preferably from 1 g to 50 g, and still more preferably from 2 g to 20 g are provided.

The absorbent article using the particulate water absorbing agent which can be used in the invention can be obtained, for example, by molding the particulate water absorbing agent and a hydrophilic fiber if necessary into a sheet shape and the like. The absorbent article can be obtained by fixing the particulate water absorbing agent having a particle shape on paper or nonwoven fabric in a case in which the hydrophilic fiber cannot be used.

The content (core concentration) of the particulate water absorbing agent in such an absorbent article is, for example, preferably from 10 to 100% by weight, more preferably from 30 to 100% by weight, and still more preferably from 50 to 100% by weight. In addition, it is desirable to adjust the absorbent article so as to have a density in a range of from 0.06 to 0.5 (g/ml) and a basis weight in a range of from 0.01 to 0.2 (g/cm$^2$). Incidentally, examples of the fiber base material to be used may include pulverized wood pulp, cotton linters, or crosslinked cellulose fibers, hydrophilic fibers such as rayon, cotton, wool, acetate, and vinylon, and the like, and any airlaid product thereof is preferable.

In addition, according to the invention, a method for manufacturing an absorbent article is also provided which includes a step of preparing the filled particulate water absorbing agent of the invention.

EXAMPLES

Hereinafter, preferred embodiments of the invention will be described in more detail using Examples, but the technical scope of the invention should not be construed as being limited only to the following Examples.

Production Example 1-1 of Particulate Water Absorbing Agent

The particulate water absorbing agent was produced by conducting the same operation as in Example 3 described in WO 2011/126079 using a continuous production apparatus which was able to continuously carry out the respective steps since the respective apparatuses for carrying out the polymerizing step, the gel grain refining (cracking) step, the drying step, the pulverizing step, the classifying step, the surface crosslinking step (spraying step and heating step of surface cross linking agent), the cooling step, the sizing step, and the product storage/fill ing step were connected by a transport apparatus. However, the same amount of ethylene carbonate was used instead of 1,4-butanediol used as a surface crosslinking agent at this time.

A particulate water absorbing agent (a-1) which had a mass average particle size (D50) of about 370 μm, and the logarithmic standard deviation (σξ) of the particle size distribution was about 0.34, and was subjected to the sizing was obtained in this manner. The centrifuge retention capacity (CRC) of this particulate water absorbing agent (a-1) was 26.8 (g/g), the absorbency against pressure (AAP) thereof was 23.9 (g/g), the saline flow conductivity (SFC) thereof was 98 ($\times 10^{-7} \cdot cm^3 \cdot s \cdot g^{-1}$), and the free swell rate (FSR) thereof was 0.38 (g/g/s). In addition, the bulk specific gravity of the particulate water absorbing agent (a-1) was 0.60 (g/ml).

Production Example 2-1 of Particulate Water Absorbing Agent

A particulate water absorbing agent (b–1) (AAP=23.0 (g/g), SPC=45.0 ($\times 10^{-7} \cdot cm^3 \cdot s \cdot g^{-1}$)) was produced in accordance with the production example of the particulate water absorbing agent described in Patent Literature 13 (WO 2009/113671 A). The free swell rate (FSR) of the particulate water absorbing agent (b–1) was measured, and the result was 0.24 (g/g/s).

Experimental Example 1-1

The filling of the particulate water absorbing agent (a) obtained in Production Example 1-1 above was conducted using the filling apparatus illustrated in FIG. 1. Incidentally, material for the hanging belt 20 is a fabric, and the hanging belt 20 has a structure to allow play at the contact portion with the filling container 16 and to allow play at the contact portion with the hanging portion 22 (hereinafter, the same applies).

The vibration generator was constituted by two unbalanced mass-type vibration generators, and the rotational directions of the vibration motors were set to be reverse to each other in order to set the cycles to be reverse to each other so that the vibrational angle was 90°±5° for the purpose of suppressing the vibration in the horizontal direction.

The vibrating body was set such that the vibration at no load had an amplitude of 0.28 (mm), a vibration frequency of 60 [Hz], an acceleration of 2.0 [G], and a vibration index of 27.1. In addition, the vibration was a linear vibration, and the vibrational angle was in the range of 90°±5°. Incidentally, the "amplitude" is synonymous with the "total amplitude", and it is the same in the section of Examples. Incidentally, the pallet is made of wood, the size thereof is 110 cm in length and 110 cm in width, and the weight thereof is 18.6 kg.

The relative humidity of the surroundings (surrounding atmosphere) of the filling apparatus was set to 60% by air conditioning. Before filling, the flexible container bag was inflated with dry air (dew point of –30° C.), and dry air was filled in the internal apace of the flexible container bag. Subsequently, as illustrated in FIG. 1, the flexible container bag was set so as to come into contact with the top of the pallet. The flexible container bag had a capacity of 1600 liters, a flexible container bag having a two-layer structure in which the inner layer was a film formed of polyethylene and the outer layer was a woven fabric formed of polypropylene was used.

Next, the filling step was carried out. The supply was conducted by dividing into two times.

First, 940 kg of the particulate water absorbing agent (a-1) was introduced into the flexible container bag in the first supply. More specifically, the vibrating step was started at the time point in 40 seconds (W1=about 537 kg) after the first supply was started. The time required for the first supply was 70 seconds, and the vibrating step was also ended at the same time as the end of the first supply (namely, the time point of W1=940 kg).

The second supply was started after a lapse of 10 seconds from the end of the first supply. The time for the second supply was 50 seconds. In this second supply, 60 kg of the particulate water absorbing agent (a-1) was introduced (namely, the final filling amount W2=1000 kg). The vibrating step was not carried out while the second supply was being conducted. Hence, the vibration time was 30 seconds.

The temperature of the particulate water absorbing agent during the vibrating step was from 40° C. to 50° C. Incidentally, the temperature of the surroundings of the filling apparatus was set from 20° C. to 30° C. In addition, the relative humidity in the space portion within 30 cm from the surface of the particulate water absorbing agent was 30% RH.

The shape of the flexible container bag after filling became approximately cylindrical as the particulate water absorbing agent was filled, the height of the filled particulate water absorbing agent was 145 cm, and the diameter of the horizontal plane thereof was approximately a circle to be about 110 cm.

The particulate water absorbing agent at the part that is 20 cm deep from the top of the bag after filling was sampled and adopted as the "particulate water absorbing agent (1-1) after filling". This flexible container bag was loaded on a truck and transported about 5 km, and the particulate water absorbing agent at the part that was 20 cm deep from the top of the bag was then sampled again and adopted as the "particulate water absorbing agent (1-1) after transport".

Experimental Example 2-1

The same operation as in Experimental Example 1-1 was conducted by changing the vibration condition as follows.

The vibration generator was constituted by two unbalanced mass-type vibration generators, and the rotational directions of the vibration motors were set to be reverse to each other in order to set the cycles to be reverse to each other so that the vibrational angle was 90°±5° for the purpose of suppressing the vibration in the horizontal direction. The vibrating body was set such that the vibration at no load had an amplitude of 1.10 ([m], a vibration frequency of 30 [Hz], an acceleration of 2.0 [G], and a vibration index of 35.8. In addition, the vibration was a linear vibration, and the vibrational angle was in the range of 90±5°. The pallet is made of a plastic, the size thereof is 110 cm in length and 110 cm in width, and the weight thereof is 10.4 kg.

The "particulate water absorbing agent (2-1) after filling" and the "particulate water absorbing agent (2-1) after transport" were obtained by conducting the sampling and the transport in the same manner as in Experimental Example 1-1.

Experimental Example 3-1

The same operation as in Experimental Example 1-1 was conducted by changing the vibration condition as follows.

The vibration generator was constituted by two unbalanced mass-type vibration generators, and the rotational directions of the vibration motors were set to be reverse to each other in order to set the cycles to be reverse to each other so that the vibrational angle was 90°±5° for the purpose of suppressing the vibration in the horizontal direction. The vibrating body was set such that the vibration at no load had an amplitude of 3.81 [mm], a vibration frequency of 30 (Hz), an acceleration of 6.9 [G], and a vibration index of 41.9. In addition, the vibration was a linear vibration, and the vibrational angle was in the range of 90°±5°. The pallet is made of wood, the size thereof is 110 cm in length and 110 cm in width, and the weight thereof is 18.6 kg.

The "particulate water absorbing agent (3-1) after filling" and the "particulate water absorbing agent (3-1) after transport" were obtained by conducting the sampling and the transport in the same manner as in Experimental Example 1-1.

Experimental Example 4-1

The same operation as in Experimental Example 1-1 was conducted by changing the vibration condition as follows.

The vibration generator was constituted by two unbalanced mass-type vibration generators, and the rotational directions of the vibration motors were set to be reverse to each other in order to set the cycles to be reverse to each other so that the vibrational angle was 90°±5° for the purpose of suppressing the vibration in the horizontal direction. The vibrating body was set such that the vibration at no load had an amplitude of 4.52 [mm], a vibration frequency of 30 (Hz), an acceleration of 8.2 [G], and a vibration index of 43.5. In addition, the vibration was a linear vibration, and the vibrational angle was in the range of 90°±5°. The pallet is made of wood, the size thereof is 110 cm in length and 110 cm in width, and the weight thereof is 18.6 kg.

The "particulate water absorbing agent (4-1) after filling" and the "particulate water absorbing agent (4-1) after transport" were obtained by conducting the sampling and the transport in the same manner as in Experimental Example 1-1.

Comparative Example 1-1

The same operation as in Experimental Example 1-1 was carried out without conducting vibration.

The "comparative particulate water absorbing agent (1-1) after filling" and the "comparative particulate water absorbing agent (1-1) after transport" were obtained by conducting the sampling and the transport in the same manner as in Experimental Example 1-1.

Comparative Example 2-11

The same operation as in Experimental Example 1-1 was conducted by changing the vibration condition as follows.

The vibration generator was constituted by two unbalanced mass-type vibration generators, and the rotational directions of the vibration motors were set to be reverse to each other in order to set the cycles to be reverse to each other so that the vibrational angle was 90°±5° for the purpose of suppressing the vibration in the horizontal direction. The vibrating body was set such that the vibration at no load had an amplitude of 0.18 [mm], a vibration frequency of 60 (Hz), an acceleration of 1.3 [G], and a vibration index of 26.2. In addition, the vibration was a linear vibration, and the vibrational angle was in the range of 90°±5°. The pallet is made of wood, the size thereof is 110 cm in length and 110 cm in width, and the weight thereof is 18.6 kg.

The "comparative particulate water absorbing agent (2-1) after filling" and the "comparative particulate water absorbing agent (2-1) after transport" were obtained by conducting the sampling and the transport in the same manner as in Experimental Example 1-1.

Comparative Example 3-1

The same operation as in Experimental Example 1-1 was conducted by changing the vibration condition as follows.

The vibration generator was constituted by two unbalanced mass-type vibration generators, and the rotational directions of the vibration motors were set to be reverse to each other in order to set the cycles to be reverse to each other so that the vibrational angle was 90°±5° for the purpose of suppressing the vibration in the horizontal direction. The vibrating body was set such that the vibration at no load had an amplitude of 5.57 [mm], a vibration frequency of 30 [Hz], an acceleration of 10.1 [G], and a vibration index of 45.8. In addition, the vibration was a linear vibration, and the vibrational angle was in the range of 90°±5°. The pallet is made of wood, the size thereof is 110 cm in length and 110 cm in width, and the weight thereof is 18.6 kg.

In the present Comparative Example, the pallet was broken during the vibrating step. The pallet was replaced after the filling operation, and the sampling and the transport were conducted in the same manner as in Experimental Example 1-1, thereby obtaining the "comparative particulate water absorbing agent (3-1) after filling" and the "comparative particulate water absorbing agent (3-1) after transport".

For the particulate water absorbing agents (1-1) to (4-1) and the comparative particulate water absorbing agents (1-1) to (3-1) "after filling" and the particulate water absorbing agents (1-1) to (4-1) and the comparative particulate water absorbing agents (1-1) to (3-1) "after transport" which were obtained in Experimental Examples 1-1 to 4-1 and Comparative Examples 1-1 to 3-1 above, the weight ratio of the particles larger than 300 μm to the particles smaller than 300 μm was determined using a JIS sieve (JIS Z8801-1) with a mesh size of 300 μm. The ratio of above to below 300 μm for each of the particulate water absorbing agents and the comparative particulate water absorbing agents "after filling" and the particulate water absorbing agents and the comparative particulate water absorbing agents "after transport" are presented in the following Table 1-1. Incidentally, for example, the notation of 75/25 indicates that the proportion of the particles larger than 300 μm is 75% by weight and the proportion of the particles smaller than 300 μm is 25% by weight.

effect which has not been exhibited in the prior art is exhibited in the particulate water absorbing agent having a high water absorbing speed (FSR of 0.25 or more) by filling the particulate water absorbing agent under a vibration condition (acceleration of from 1 G to 13 G and vibration index in a range of from 27 to 44) different from that in Patent Literature 13 and also by significantly suppressing the vibration in the horizontal direction. In other words, in the case of producing a particulate water absorbing agent having a high water absorbing speed (PSR of 0.25 or more), it is preferable to contain a particulate water absorbing agent having a significantly large surface area (those having a small particle size) as well, and thus, the segregation tends to occur. On the contrary, it is indicated that it is possible to suppress the segregation according to the invention since there is little difference between the ratios of above to below for the particulate water absorbing agent "after filling" and the particulate water absorbing agent "after transport" even in such an embodiment in which the segregation is likely to occur.

Production Example 1-2 of Particulate Water Absorbing Agent

The filled particulate water absorbing agent was fabricated by fabricating the particulate water absorbing agent (a-2) and filling it in the same manner as in Production Example 1-1 of particulate water absorbing agent. Incidentally, in the same manner as in Production Example 1-1, the shape of the flexible container bag after filling became approximately cylindrical as the particulate water absorbing agent was filled, the height of the filled particulate water absorbing agent was 145 cm, and the diameter of the horizontal plane thereof was approximately a circle to be about 110 cm.

Experimental Examples 1-2 to 6-2

This flexible container bag was loaded on a truck and transported about 5 km, and the particulate water absorbing

TABLE 1-1

| | Amplitude [mm] | Frequency [Hz] | Acceleration [G] | Vibration index | Ratio of above to below 300 μm for particulate water absorbing agent after filling [wt %]/[wt %] | Ratio of above to below 300 μm for particulate water absorbing agent after transport [wt %]/[wt %] |
|---|---|---|---|---|---|---|
| Comparative Example 1-1 | — | — | — | — | 74/26 | 82/18 |
| Comparative Example 2-1 | 0.18 | 60 | 1.3 | 26.2 | 76/24 | 82/18 |
| Experimental Example 1-1 | 0.28 | 60 | 2.0 | 27.1 | 75/25 | 79/21 |
| Experimental Example 2-1 | 1.10 | 30 | 2.0 | 35.8 | 76/24 | 77/23 |
| Experimental Example 3-1 | 3.81 | 30 | 6.9 | 41.9 | 76/24 | 77/23 |
| Experimental Example 4-1 | 4.52 | 30 | 8.2 | 43.5 | 77/23 | 79/21 |
| Comparative Example 3-1 | 5.57 | 30 | 10.1 | 45.8 | 77/23 | 82/18 |

From the results presented in Table 1-1, it can be seen that the segregation can be suppressed not only after filling but also after transport. In other words, it can be seen that an agent was then sampled from the top of the flexible container bag using a sampler. The sampler has a total length of 150 cm and is a double tube which is made of SUS and has a sampling window attached to the tip. The inserted depth was 20 cm, 60 cm, and 100 cm based on the center of the sampling window, and about 150 g of sample was taken at three points having different depths in the vertical direction. In addition, the point where the sampler was inserted was the center of the cross-sectional area in the horizontal direction and four points were evenly disposed at every 90 degrees and denoted as "front", "back", "right", and "left" for convenience) on the outer side by 35 cm in the outer circumferential direction. The particulate water absorbing agent was obtained from 15 different points in the flexible container bag in this manner. This operation was conducted for six flexible container bags. The obtained physical properties of the particulate water absorbing agent are presented in Table 1 to 6. Incidentally, the bulk specific gravity in Tables 2 to 7 is for the particulate water absorbing agent sampled in only the top center. This is because the bulk specific gravity is not a water absorption physical property value and the sample taken in the top center is judged to be regarded as a value representing the entire from the results in Table 1.

Experimental Example 7-2

The particulate water absorbing agent was obtained from the 15 points by conducting the same operation as in Experimental Example 1-2 except that the vibrating step was not carried out. The obtained physical properties of the water absorbing agent are presented in Table 7. In addition, the physical properties of the water absorbing agents of Experimental Example 1-2 to Experimental Example 7-2 are compared with one another in Table 11.

Experimental Example 8-2

As model verification experiment of Experimental Examples 1-2 to 6-2 and Experimental Example 7-2, the following experiment was subsequently conducted. Incidentally, during the experimental operation, the vibration by a micro-type electromagnetic vibrator is an operation that models the vibrating step in Experimental Examples 1-2 to 6-2, and shaking by a large low tap shaker is an operation that models the impact to the container at the time of transport by a truck in Experimental Examples 1-2 to 7-2.

First, in order to confirm that the particulate water absorbing agent is sufficiently uniformly filled before vibration and shaking, an outer container which has a sampling hole (diameter of 21 mm, the center is positioned at 10 mm (bottom part), 70 mm (central part), and 140 mm (top part) from the bottom surface) on the side of a polyethylene wide-mouthed plastic bottle (capacity described in catalog: 2 L, real effective capacity: 2255 cm$^3$, A-6000 GENERAL CATALOGUE 2011, product code: 616-09 manufactured by SOGO LABORATORY GLASS WORKS CO., LTD.) was fabricated as the outer packaging. In addition, a polyethylene plastic bag (0.03 mm thick, 450 mm long, and 300 mm wide) was inserted into the outer container as the inner packaging, and the inner packaging was inflated with dry air (dew point temperature: −30° C.), thereby fabricating the filling container.

Into the filling container, 1.5 kg of the particulate water absorbing agent (a-2) obtained in Production Example 1-2 was introduced over 90 seconds at one time, the lid was put on the inner packaging and the outer packaging, the particulate water absorbing agent was then stirred and mixed for 60 minutes by rotating and tipping movement using Shaker-Mixer (TURBULA (registered trademark) Type T2F manufactured by Willy A. Bachofen AG Maschinenfabrik Basel) to homogenize the particulate water absorbing agent in the filling container. The volume of the particulate water absorbing agent (a-2) after stirring was 2209 cm$^3$. In addition, the relative humidity in the space portion within 30 cm from the surface of the particulate water absorbing agent was 45% RH.

Incidentally, the vibration by Shaker-Mixer is simply a rotating and tipping movement, it is conducted for the purpose of homogenizing the particulate water absorbing agent in the filling container, and it is different from the vibration condition of the micro-type electromagnetic vibrator used in Experimental Example 9-2 and the like.

The filling container was allowed to stand after stirring, a metal pipe (cork borer No. 11, A-6000 GENERAL CATALOGUE 2011, product code: 2788-03 manufactured by SOGO LABORATORY GLASS WORKS CO., LTD.) having an outer diameter of 20 am and an inner diameter of 19 mm was inserted into the side sampling hole by about 6 cm, and about 20 g of the particulate water absorbing agent was taken. Incidentally, the sampling was conducted in order from the top of the sampling hole, and the open hole was closed with adhesive tape after sampling so as to suppress the efflux of the particulate water absorbing agent from the filling container. The obtained physical properties of the water absorbing agent are presented in Table 8.

Incidentally, it can be seen that the relative standard deviations of the respective physical properties are significantly small even without using the filling method of the invention since Experimental Example 8-2 is a model of the stage of (I) (namely, before transport).

Experimental Example 9-2

The filling container after stirring by Shaker-Mixer (namely, final filling amount W2=1.5 kg) was obtained by conducting the same operation as in Experimental Example 8-2. The filling container thus obtained was fixed on a micro-type electromagnetic vibrator (M-3T manufactured by TSUTSUI SCIENTIFIC INSTRUMENTS CO., LTD.) and vibrated for 30 seconds. In other words, the vibration of the invention was applied at the time of W1/W2=100.

The vibration condition was that the amplitude (at no load) was 2 mm, the vibration frequency (at no load) was 60 Hz, the acceleration was 14.5 G, and the vibration index was 42.6 for the vibration at no load, and the vibrational angle was 90°±5°. In addition, it was linear vibration. Incidentally, the "vibration at no load" as used herein refers to a state in which any of the sample, the container, or the like is not mounted on the vibrator in the same manner as above. In addition, the temperature of the particulate water absorbing agent during the vibrating step was from 40° C. to 50° C.

The volume of the particulate water absorbing agent (a-2) after vibration was 2086 cm$^3$. The sample was taken from the filling container after vibration thus obtained in the same manner as Experimental Example 8-2. The obtained physical properties of the water absorbing agent are presented in Table 8.

Experimental Example 10-2

The filling container after vibration was obtained by conducting the same operation as in Experimental Example 9-2.

The inner packaging of the filling container thus obtained was once opened, the air of the part where the water absorbing agent is not filled was extruded, the inner packaging and the outer packaging were sealed again, this filling container was mounted on a large low tap shaker (model RH-1 manufactured by Tanaka Tec CO., LTD.) and shaken (shaking speed of horizontal elliptical motion of 300 rpm, shaking width of 25 mm, and hammer hitting number of 150 tapping/min) for 10 minutes, and the sampling was then conducted in the same manner as in Experimental Example 8-2. The volume of the water absorbing agent (a-2) after shaking for 10 minutes but before sampling was 2025 cm$^3$. The obtained physical properties of the water absorbing agent are presented in Table 8.

Thereafter, the filling container was fixed by being diagonally inclined. Furthermore, the metal pipe (cork borer No. 11) described in Experimental Example 8-2 was inserted into the bottom sampling hole by about 1 cm to continuously discharge the water absorbing agent while dropping the water absorbing agent by gravity.

The time required until the discharge from the filling container stopped was about 80 seconds, and each of the dropping water absorbing agent was taken by about 20 g after 5 seconds and after 50 seconds from the start of discharge. The obtained physical properties of the water absorbing agent are presented in Table 10.

In addition, the filling container after being shaken for 10 minutes by a large low tap shaker was obtained by repeating the above operation again in order to measure the bulk specific gravity of the particulate water absorbing agent in filled product. The particulate water absorbing agent in the inside was taken by about 150 g only from the central part of sampling hole of the filling container thus obtained, the bulk specific gravity thereof was measured, and the result was 0.60 (g/ml).

Experimental Example 11-2

In Experimental Experiment 10-2, the shaking was conducted for 10 minutes by a large low tap shaker without conducting the vibration by a micro-type electromagnetic vibrator, and the sampling was conducted in the same manner as in Experimental Example 8-2. The obtained physical properties of the water absorbing agent are presented in Table 6.

Here, in Table 8, Experimental Examples 8-2, 10-2, and 11-2 are compared with one another. In Experimental Example 8-2, it can be seen that the relative standard deviations of the respective water absorption physical property values are significantly low although the vibration by a micro-type electromagnetic vibrator was not conducted. This is because the shaking that is a model of truck transport was not conducted. However, as presented in Experimental Example 11-2, it can be seen that the relative standard deviations of the respective water absorption physical property values increase when the shaking (jolting at the time of truck transport is applied) is once conducted. In other words, this indicates that variations of the water absorption physical property values of the respective final products (absorbent articles) can be caused. On the other hand, in Experimental Example 10-2, the vibration by a micro-type electromagnetic vibrator is conducted, and thus the relative standard deviation is low even though the shaking that is a model of the truck transport is conducted. In other words, it indicates that variations of the water absorption physical property values of the respective final products (absorbent articles) are significantly suppressed.

Thereafter, the dropping water absorbing agent was taken by about 20 g for each while continuously discharging the water absorbing agent in the same manner as in Experimental Example 10-2. The obtained physical properties of the water absorbing agent are presented in Table 10. Incidentally, the time required until the discharge stopped was about 80 seconds.

Production Example 2-2 of Particulate Water Absorbing Agent

The particulate water absorbing agent (b-2) was produced in accordance with the product ion example of the particulate water absorbing agent described in WO 2009/113671. The bulk specific gravity was 0.64 (g/ml) when about 1 kg of the particulate water absorbing agent (b-2) was homogenized by sufficiently stirring it and 100 g thereof was then taken and subjected to the measurement. The AAP, SFC, and PSR of the particulate water absorbing agent (b-2) were the same as those of the particulate water absorbing agent (b-1).

Experimental Example 12-2

The sampling was conducted by conducting the same operation as in Experimental Example 10-2 except that the particulate water absorbing agent used was changed from the water absorbing agent (a-2) to the water absorbing agent (b-2). The obtained physical properties of the water absorbing agent are presented in Table 8.

Experimental Example 13-2

The sampling was conducted by conducting the same operation as in Experimental Example 11-2 except that the particulate water absorbing agent used was changed from the water absorbing agent (a-2) to the water absorbing agent (b-2). The obtained physical properties of the water absorbing agent are presented in Table 8.

As presented in Table 8, it can be seen that the relative standard deviations in Experimental Example 12-2 are smaller than those in Experimental Example 13-2, and the water absorbing agent exhibits excellent stability.

Production Example 3-2 of Particulate Water Absorbing Agent

In a reactor formed by attaching a lid to a jacketed stainless twin-arm kneader having two sigma-type blades and an internal volume of 10 liters, 7.1 g (0.06% by mole) of polyethylene glycol diacrylate was dissolved in 5432.0 g (monomer concentration of 39% by weight) of an aqueous solution of sodium acrylate having a neutralization rate of 73% by mole to obtain the reaction liquid. Next, this reaction liquid was degassed for 30 minutes under a nitrogen gas atmosphere. Subsequently, 29.36 g of an aqueous solution of sodium persulfate at 10% by weight and 24.5 g of an aqueous solution of L-ascorbic acid at 0.1% by weight were added to the above reaction liquid while stirring. The polymerization started in about 1 minute after the addition. Thereafter, the polymerization was conducted at from 20° C. to 95° C. while crushing the generated gel, and the hydrogel-like crosslinked polymer was taken out in 30 minutes after the polymerization started. The hydrogel-like crosslinked polymer thus obtained had been fragmented to have a particle size of about 5 mm or less. The hydrogel-like crosslinked polymer that had been crushed and fragmented was spread on a wire mesh of 50 meshes (mesh size of 300 μm) and dried with hot air at 180° C. for 50 minutes. The water absorbent resin thus obtained was pulverized using a roll mill and further classified with JIS standard sieves having a mesh size of 850 μm and 106 μm to adjust the particle size distribution, thereby obtaining a water absorbent resin.

Subsequently, 3.7 parts by weight of an aqueous solution of surface crosslinking agent composed of 0.2 part by weight of ethylene glycol diglycidyl ether, 0.5 part by weight of 1,2-propanediol, and 3 parts by weight of ion exchanged water was sprayed to 100 parts by weight of the water absorbent resin thus obtained and stirred at a high speed to mix. The mixture thus obtained was introduced into a paddle-type dryer having a heat medium temperature of 200° C., then taken out after the stirring and heating treatment for 40 minutes, and cooled, thereby obtaining a water absorbent resin having a crosslinked surface. To 100 parts by weight of this water absorbent resin having a crosslinked surface, 0.1 part by weight of an aqueous solution of polyoxyethylene (20) sorbitan monostearate at 10% by weight (manufactured by Kao Corporation) was sprayed and mixed, thereby obtaining the particulate water absorbing agent (c-2). The bulk specific gravity was 0.72 (g/ml) when about 1 kg of the particulate water absorbing agent (c-2) obtained by repeating this operation was homogenized by sufficiently stirring it and 100 g thereof was then taken and subjected to the measurement.

Experimental Example 14-2

The sampling was conducted by conducting the same operation as in Experimental Example 8-2 except that the particulate water absorbing agent used was changed from the water absorbing agent (a-2) to the water absorbing agent (c-2). The obtained physical properties of the water absorbing agent are presented in Table 9. Incidentally, it can be seen that the relative standard deviations of the respective physical properties are significantly small even without using the filling method of the invention since Experimental Example 14-2 is a model of the stage of (I) (namely, before transport) above.

Experimental Example 15-2

The sampling was conducted by conducting the same operation as in Experimental Example 10-2 except that the particulate water absorbing agent used was changed from the water absorbing agent (a-2) to the water absorbing agent (c-2). The obtained physical properties of the water absorbing agent are presented in Table 9.

Thereafter, the dropping water absorbing agent was taken by about 20 g for each while continuously discharging the water absorbing agent in the same manner as in Experimental Example 10-2. Incidentally, the time required until the discharge stopped was about 75 seconds. The obtained physical properties of the water absorbing agent are presented in Table 10.

In addition, the filling container after being shaken for 10 minutes by a large low tap shaker was obtained by repeating the above operation again in order to measure the bulk specific gravity of the particulate water absorbing agent in the filled product. The particulate water absorbing agent in the inside was taken by about 150 g only from the central part of sampling hole of the filling container thus obtained, the bulk specific gravity thereof was measured, and the result was 0.72 (g/ml).

Experimental Example 16-2

In Experimental Experiment 15-2, the shaking was conducted for 10 minutes by a large low tap shaker without conducting the vibration by a micro-type electromagnetic vibrator, and the sampling was conducted in the same manner as in Experimental Example 8-2. The obtained physical properties of the water absorbing agent are presented in Table 9.

Thereafter, the dropping water absorbing agent was taken by about 20 g for each while continuously discharging the water absorbing agent in the same manner as in Experimental Example 10-2. The obtained physical properties of the water absorbing agent are presented in Table 10. The time required until the discharge stopped was about 75 seconds.

As presented in Table 9, it can be seen that the relative standard deviations in Experimental Example 15-2 are smaller than those in Experimental Example 16-2, and the water absorbing agent exhibits excellent stability.

Incidentally, in Table 12, a table summarizing the relation among Experimental Example 1-2 to Experimental Example 1-16 is presented.

Comparative Example 1-2

When the average value and the standard deviation when N values are arbitrarily selected from the SPC values for 15 points in Experimental Example 7-2 are denoted as Ave (N) and σ (N), respectively, the values which are out of the range of Ave (N)±σ (N) among the values for the points are denoted as OUT (N), and the following results are obtained.

$$2 \leq OUT(10) \leq 9$$

$$3 \leq OUT(11) \leq 6$$

$$3 \leq OUT(12) \leq 6$$

$$4 \leq OUT(13) \leq 5$$

$$4 \leq OUT(14) \leq 5$$

$$OUT(15)=5$$

To have a small value of OUT (N) means that the dispersion of the population is estimated to be great, but to have a great value of OUT (N) means that the dispersion of the population is estimated to be small. In other words, it can be seen that it is highly possible to evaluate the variation in performance in the filling container differently from the true variation when N is less than 13.

<Method for Deriving Equation 4>

As described above, Equation 4 is as follows:

[Mathematical Formula 25]

$$\text{Vibration index}=42-0.29 \times \text{vibration frequency at no load [Hz]}+1.24 \times \text{acceleration [G]} \quad \text{(Equation 4)}$$

Equation 4 was derived as follows.

In other words, in order to set the vibration condition (vibration frequency at no load (Hz) and acceleration (G)) before conducting the filling of the particulate water absorbing agent using the filling apparatus illustrated in FIG. 1, the filling apparatus was run in a state in which 16 (filling container) and 26 (pallet) of FIG. 1 were not mounted, that is, in a state in which nothing was mounted on 10 and 12 (vibrating body) of FIG. 1.

As a result, the set value consisting of from 10 to 90 for the vibration frequency at no load (Hz) and from 1 to 15 for the acceleration (G) was obtained as the vibration condition. Subsequently, the filling container containing the particulate water absorbing agent was vibrated at the set value to confirm the volume reduction effect.

Using the data obtained in the above operation, the multiple regression analysis was performed by adopting the "volume reduction effect" as the "objective variable" and the "vibration frequency at no load" and the "acceleration" as the explanatory variable using the Excel (registered trademark) developed by Microsoft Corporation.

As a result, "42" was obtained as the intercept, "−0.29" was obtained as the constant of the "vibration frequency at no load (Hz)", and "1.24" was obtained as the constant of the "acceleration".

TABLE 1

Experimental Example 1-2

|  |  | CRC [g/g] | AAP [g/g] | FSR [g/g/s] | SFC [(1)] | Bulk specific gravity [g/ml] |
|---|---|---|---|---|---|---|
| Top part | Center | 27.2 | 24.1 | 0.38 | 95 | 0.60 |
|  | Front | 27.5 | 24.0 | 0.35 | 100 | 0.60 |
|  | Back | 27.6 | 24.0 | 0.34 | 98 | 0.59 |
|  | Left | 27.1 | 24.0 | 0.36 | 95 | 0.60 |
|  | Right | 27.4 | 24.0 | 0.34 | 97 | 0.59 |
| Central part | Center | 27.5 | 24.0 | 0.38 | 92 | 0.60 |
|  | Front | 27.4 | 24.0 | 0.35 | 108 | 0.61 |
|  | Back | 27.1 | 23.9 | 0.37 | 104 | 0.60 |
|  | Left | 27.5 | 24.1 | 0.33 | 101 | 0.59 |
|  | Right | 27.5 | 23.9 | 0.35 | 99 | 0.60 |
| Bottom part | Center | 27.4 | 24.1 | 0.37 | 90 | 0.62 |
|  | Front | 27.2 | 24.0 | 0.36 | 95 | 0.62 |
|  | Back | 27.3 | 23.0 | 0.38 | 96 | 0.60 |
|  | Left | 27.4 | 24.0 | 0.36 | 98 | 0.61 |
|  | Right | 27.4 | 24.0 | 0.34 | 87 | 0.60 |
| Average |  | 27.4 | 24.0 | 0.36 | 97 | 0.60 |
| Standard deviation |  | 0.15 | 0.08 | 0.016 | 5.3 | 0.009 |
| Relative standard deviation |  | 0.6% | 0.3% | 4.5% | 5.4% | 1.6% |

(1): [×10$^{-7}$ · cm$^7$ · g · s$^{-1}$]

TABLE 2

Experimental Example 2-2

|  |  | CRC [g/g] | AAP [g/g] | FSR [g/g/s] | SFC [(1)] | Bulk specific gravity [g/ml] |
|---|---|---|---|---|---|---|
| Top part | Center | 26.8 | 24.0 | 0.37 | 95 | 0.58 |
|  | Front | 27.3 | 24.0 | 0.38 | 95 |  |
|  | Back | 26.7 | 23.9 | 0.41 | 98 |  |
|  | Left | 27.0 | 24.1 | 0.38 | 91 |  |
|  | Right | 27.0 | 24.0 | 0.40 | 98 |  |
| Central part | Center | 27.2 | 24.0 | 0.37 | 95 |  |
|  | Front | 26.8 | 24.1 | 0.37 | 92 |  |
|  | Back | 27.2 | 24.0 | 0.38 | 91 |  |
|  | Left | 27.4 | 24.1 | 0.37 | 96 |  |
|  | Right | 27.0 | 23.9 | 0.39 | 92 |  |
| Bottom part | Center | 26.7 | 23.9 | 0.38 | 93 |  |
|  | Front | 27.1 | 23.8 | 0.39 | 95 |  |
|  | Back | 26.8 | 23.8 | 0.38 | 92 |  |
|  | Left | 26.7 | 24.0 | 0.39 | 93 |  |
|  | Right | 27.1 | 23.8 | 0.39 | 94 |  |
| Average |  | 27.0 | 24.0 | 0.38 | 94 |  |
| Standard deviation |  | 0.23 | 0.11 | 0.012 | 2.3 |  |
| Relative standard deviation (%) |  | 0.9% | 0.4% | 3.1% | 2.4% |  |

(1): [×10$^{-7}$ · cm$^3$ · g · s$^{-1}$]

TABLE 3

Experimental Example 3-2

|  |  | CRC [g/g] | AAP [g/g] | FSR [g/g/s] | SFC [(1)] | Bulk specific gravity [g/ml] |
|---|---|---|---|---|---|---|
| Top part | Center | 27.6 | 24.0 | 0.35 | 96 | 0.60 |
|  | Front | 27.2 | 24.0 | 0.39 | 97 |  |
|  | Back | 27.5 | 24.0 | 0.37 | 95 |  |
|  | Left | 27.4 | 24.0 | 0.37 | 96 |  |
|  | Right | 27.3 | 23.9 | 0.39 | 96 |  |
| Central part | Center | 27.2 | 24.0 | 0.38 | 103 |  |
|  | Front | 27.4 | 24.2 | 0.36 | 102 |  |
|  | Back | 27.2 | 24.1 | 0.37 | 95 |  |
|  | Left | 26.9 | 23.9 | 0.38 | 97 |  |
|  | Right | 27.5 | 24.0 | 0.38 | 101 |  |
| Bottom part | Center | 26.8 | 24.0 | 0.37 | 96 |  |
|  | Front | 27.3 | 23.9 | 0.39 | 96 |  |
|  | Back | 27.2 | 24.0 | 0.36 | 96 |  |
|  | Left | 27.0 | 23.9 | 0.38 | 99 |  |
|  | Right | 27.1 | 23.9 | 0.38 | 95 |  |
| Average |  | 27.2 | 24.0 | 0.37 | 97 |  |
| Standard deviation |  | 0.23 | 0.08 | 0.012 | 2.6 |  |
| Relative standard deviation (%) |  | 0.8% | 0.3% | 3.2% | 2.7% |  |

(1): [×10$^{-7}$ · cm$^3$ · g · s$^{-1}$]

TABLE 4

Experimental Example 4-2

|  |  | CRC [g/g] | AAP [g/g] | FSR [g/g/s] | SFC [(1)] | Bulk specific gravity [g/ml] |
|---|---|---|---|---|---|---|
| Top part | Center | 26.7 | 24.3 | 0.35 | 101 | 0.60 |
|  | Front | 27.7 | 24.3 | 0.35 | 99 |  |
|  | Back | 27.6 | 24.2 | 0.34 | 96 |  |
|  | Left | 27.7 | 24.4 | 0.36 | 105 |  |
|  | Right | 26.9 | 24.2 | 0.36 | 95 |  |
| Central part | Center | 27.5 | 24.4 | 0.34 | 103 |  |
|  | Front | 27.3 | 24.3 | 0.35 | 96 |  |
|  | Back | 26.8 | 24.2 | 0.37 | 98 |  |
|  | Left | 27.2 | 24.0 | 0.36 | 101 |  |
|  | Right | 27.2 | 24.1 | 0.37 | 101 |  |
| Bottom part | Center | 27.5 | 24.1 | 0.36 | 98 |  |
|  | Front | 27.3 | 24.1 | 0.35 | 96 |  |
|  | Back | 26.9 | 24.0 | 0.38 | 92 |  |
|  | Left | 27.2 | 24.0 | 0.38 | 101 |  |
|  | Right | 27.0 | 24.0 | 0.37 | 92 |  |
| Average |  | 27.2 | 24.2 | 0.36 | 98 |  |
| Standard deviation |  | 0.32 | 0.14 | 0.013 | 3.8 |  |
| Relative standard deviation (%) |  | 1.2% | 0.6% | 3.6% | 3.9% |  |

(1): [×10$^{-7}$ · cm$^3$ · g · s$^{-1}$]

TABLE 5

Experimental Example 5-2

|  |  | CRC [g/g] | AAP [g/g] | FSR [g/g/s] | SFC [(1)] | Bulk specific gravity [g/ml] |
|---|---|---|---|---|---|---|
| Top part | Center | 26.8 | 23.8 | 0.39 | 94 | 0.59 |
|  | Front | 27.0 | 23.9 | 0.39 | 91 |  |
|  | Back | 26.8 | 23.8 | 0.41 | 97 |  |
|  | Left | 26.8 | 23.9 | 0.43 | 99 |  |
|  | Right | 26.9 | 23.8 | 0.39 | 96 |  |
| Central part | Center | 26.9 | 23.8 | 0.40 | 93 |  |
|  | Front | 27.2 | 23.9 | 0.38 | 94 |  |
|  | Back | 27.1 | 24.0 | 0.38 | 93 |  |

TABLE 5-continued

Experimental Example 5-2

|  |  | CRC [g/g] | AAP [g/g] | FSR [g/g/s] | SFC [(1)] | Bulk specific gravity [g/ml] |
|---|---|---|---|---|---|---|
|  | Left | 27.2 | 23.9 | 0.38 | 100 |  |
|  | Right | 26.8 | 23.7 | 0.40 | 91 |  |
| Bottom | Center | 26.8 | 23.7 | 0.39 | 92 |  |
| part | Front | 27.2 | 23.8 | 0.38 | 91 |  |
|  | Back | 27.1 | 23.8 | 0.40 | 92 |  |
|  | Left | 27.0 | 23.9 | 0.40 | 93 |  |
|  | Right | 27.0 | 23.7 | 0.39 | 94 |  |
| Average |  | 27.0 | 23.8 | 0.39 | 94 |  |
| Standard deviation |  | 0.16 | 0.09 | 0.014 | 2.8 |  |
| Relative standard deviation (%) |  | 0.6% | 0.4% | 3.4% | 3.0% |  |

(1); [×10$^{-7}$ · cm$^3$ · g · s$^{-1}$]

TABLE 6

Experimental Example 6-2

|  |  | CRC [g/g] | AAP [g/g] | FSR [g/g/s] | SFC [(1)] | Bulk specific gravity [g/ml] |
|---|---|---|---|---|---|---|
| Top part | Center | 26.8 | 24.1 | 0.37 | 101 | 0.60 |
|  | Front | 27.2 | 24.0 | 0.37 | 104 |  |
|  | Back | 27.3 | 23.9 | 0.38 | 105 |  |
|  | Left | 26.8 | 24.0 | 0.37 | 100 |  |
|  | Right | 26.4 | 23.8 | 0.36 | 109 |  |
| Central | Center | 27.1 | 24.1 | 0.38 | 95 |  |
| part | Front | 26.8 | 24.0 | 0.38 | 99 |  |
|  | Back | 27.2 | 23.9 | 0.35 | 99 |  |
|  | Left | 27.4 | 24.0 | 0.40 | 98 |  |
|  | Right | 26.9 | 23.9 | 0.38 | 107 |  |
| Bottom | Center | 27.2 | 23.9 | 0.39 | 99 |  |
| part | Front | 26.6 | 24.0 | 0.40 | 101 |  |
|  | Back | 26.6 | 23.8 | 0.39 | 96 |  |
|  | Left | 27.4 | 23.9 | 0.37 | 100 |  |
|  | Right | 26.7 | 23.9 | 0.39 | 100 |  |
| Average |  | 27.0 | 23.9 | 0.38 | 101 |  |
| Standard deviation |  | 0.32 | 0.09 | 0.014 | 3.9 |  |
| Relative standard deviation (%) |  | 1.2% | 0.4% | 3.7% | 3.9% |  |

(1); [×10$^{-7}$ · cm$^3$ · g · s$^{-1}$]

TABLE 7

Experimental Example 7-2

|  |  | CRC [g/g] | AAP [g/g] | FSR [g/g/s] | SFC [(1)] | Bulk specific gravity [g/ml] |
|---|---|---|---|---|---|---|
| Top part | Center | 27.6 | 24.3 | 0.32 | 109 | 0.60 |
|  | Front | 27.3 | 24.4 | 0.35 | 96 |  |
|  | Back | 27.5 | 24.3 | 0.32 | 100 |  |
|  | Left | 27.6 | 24.1 | 0.36 | 102 |  |
|  | Right | 27.6 | 24.4 | 0.35 | 114 |  |
| Central | Center | 26.2 | 24.0 | 0.34 | 99 |  |
| part | Front | 27.5 | 24.3 | 0.33 | 90 |  |
|  | Back | 27.6 | 23.6 | 0.34 | 96 |  |
|  | Left | 27.0 | 23.8 | 0.38 | 99 |  |
|  | Right | 25.7 | 24.0 | 0.36 | 93 |  |

TABLE 7-continued

Experimental Example 7-2

|  |  | CRC [g/g] | AAP [g/g] | FSR [g/g/s] | SFC [(1)] | Bulk specific gravity [g/ml] |
|---|---|---|---|---|---|---|
| Bottom | Center | 27.4 | 24.2 | 0.37 | 86 |  |
| part | Front | 26.7 | 23.5 | 0.40 | 100 |  |
|  | Back | 27.5 | 23.4 | 0.39 | 85 |  |
|  | Left | 25.9 | 23.5 | 0.38 | 92 |  |
|  | Right | 25.8 | 23.4 | 0.40 | 81 |  |
| Average |  | 27.0 | 23.9 | 0.36 | 96 |  |
| Standard deviation |  | 0.73 | 0.38 | 0.027 | 8.8 |  |
| Relative standard deviation (%) |  | 2.7% | 1.6% | 7.5% | 9.2% |  |

(1); [×10$^{-7}$ · cm$^3$ · g · s$^{-1}$]

TABLE 8

|  | Sampling | CRC [g/g] | AAP [g/g] | SFC [(1)] | FSR [g/g/s] |
|---|---|---|---|---|---|
| Experimental Example 8-2 | Top part | 27.2 | 23.8 | 101 | 0.36 |
|  | Central part | 27.2 | 23.7 | 103 | 0.35 |
|  | Bottom part | 27.3 | 23.8 | 104 | 0.36 |
|  | Average | 27.2 | 23.8 | 103 | 0.36 |
|  | Standard deviation | 0.00 | 0.06 | 1.5 | 0.006 |
|  | Relative standard deviation | 0.2% | 0.2% | 1.5% | 1.6% |
| Experimental Example 9-2 | Top part | 27.2 | 23.3 | 101 | 0.36 |
|  | Central part | 27.1 | 23.6 | 100 | 0.35 |
|  | Bottom part | 27.3 | 23.6 | 105 | 0.36 |
|  | Average | 27.2 | 23.5 | 102 | 0.36 |
|  | Standard deviation | 0.11 | 0.17 | 2.6 | 0.006 |
|  | Relative standard deviation | 0.4 | 0.7% | 2.6% | 1.6% |
| Experimental Example 10-2 | Top part | 27.3 | 23.8 | 104 | 0.36 |
|  | Central part | 27.2 | 23.6 | 102 | 0.35 |
|  | Bottom part | 27.2 | 23.8 | 106 | 0.36 |
|  | Average | 27.2 | 23.7 | 104 | 0.36 |
|  | Standard deviation | 0.06 | 0.12 | 2 | 0.006 |
|  | Relative standard deviation | 0.2% | 0.5% | 1.9% | 1.6% |
| Experimental Example 11- | Top part | 27.8 | 24.0 | 100 | 0.33 |
|  | Central part | 27.3 | 23.7 | 114 | 0.35 |
|  | Bottom part | 26.6 | 23.2 | 102 | 0.38 |
|  | Average | 27.2 | 23.6 | 105 | 0.35 |
|  | Standard deviation | 0.59 | 0.40 | 7.6 | 0.025 |
|  | Relative standard deviation | 2.2% | 1.7% | 7.2% | 7.1% |
| Experimental Example 12-2 | Top part | 30.1 | 24.5 | 52 | 0.24 |
|  | Central part | 30.0 | 24.5 | 51 | 0.24 |
|  | Bottom part | 30.0 | 24.5 | 53 | 0.23 |
|  | Average | 30.0 | 24.5 | 52 | 0.24 |
|  | Standard deviation | 0.06 | 0.00 | 1.0 | 0.006 |
|  | Relative standard deviation | 0.2% | 0.0% | 1.9% | 2.4% |
| Experimental Example 13-2 | Top part | 30.7 | 24.4 | 50 | 0.23 |
|  | Central part | 30.5 | 24.0 | 54 | 0.24 |
|  | Bottom part | 29.0 | 23.9 | 47 | 0.26 |
|  | Average | 30.1 | 24.1 | 50 | 0.24 |
|  | Standard deviation | 0.93 | 0.26 | 3.5 | 0.015 |
|  | Relative standard deviation | 3.1% | 1.1% | 7.0% | 6.3% |

(1); [×10$^{-7}$ · cm$^3$ · g · s$^{-1}$]

TABLE 9

| | Sampling | CRC [g/g] | AAP [g/g] | SFC [(1)] | FSR [g/g/s] |
|---|---|---|---|---|---|
| Experimental Example 14-2 | Top part | 29.2 | 23.4 | 31 | 0.23 |
| | Central part | 28.9 | 23.7 | 31 | 0.24 |
| | Bottom part | 29.2 | 23.4 | 31 | 0.23 |
| | Average | 29.1 | 23.6 | 31 | 0.24 |
| | Standard deviation | 0.17 | 0.15 | 0.6 | 0.006 |
| | Relative standard deviation | 0.6% | 0.6% | 1.9% | 2.5% |
| Experimental Example 15-2 | Top part | 29.4 | 23.4 | 31 | 0.23 |
| | Central part | 28.8 | 23.7 | 33 | 0.24 |
| | Bottom part | 29.2 | 23.3 | 30 | 0.25 |
| | Average | 29.1 | 23.5 | 31 | 0.24 |
| | Standard deviation | 0.31 | 0.21 | 1.5 | 0.01 |
| | Relative standard deviation | 1.1% | 0.9% | 4.8% | 4.2% |
| Experimental Example 16-2 | Top part | 29.6 | 23.8 | 31 | 0.23 |
| | Central part | 28.2 | 23.3 | 31 | 0.24 |
| | Bottom part | 29.6 | 23.4 | 28 | 0.26 |
| | Average | 29.1 | 23.5 | 30 | 0.24 |
| | Standard deviation | 0.81 | 0.26 | 1.7 | 0.015 |
| | Relative standard deviation | 2.8% | 1.1% | 5.7% | 6.3% |

(1): [×10$^{-7}$ · cm$^3$ · g · s$^{-1}$]

TABLE 10

| | Sampling | CRC [g/g] | AAP [g/g] | SFC [(1)] | FSR [g/g/s] |
|---|---|---|---|---|---|
| Experimental Example 10-2 | 5 seconds | 27.2 | 23.7 | 105 | 0.36 |
| | 50 seconds | 27.2 | 23.8 | 102 | 0.35 |
| | Difference | 0 | 0.1 | 3 | 0.01 |
| Experimental Example 11-2 | 5 seconds | 26.5 | 23.4 | 95 | 0.38 |
| | 50 seconds | 27.9 | 24.1 | 106 | 0.32 |
| | Difference | 1.4 | 0.7 | 11 | 0.06 |
| Experimental Example 15-2 | 5 seconds | 29.2 | 23.4 | 33 | 0.24 |
| | 50 seconds | 29.1 | 23.5 | 33 | 0.23 |
| | Difference | 0.1 | 0.1 | 0 | 0.01 |
| Experimental Example 16-2 | 5 seconds | 29.6 | 23.5 | 27 | 0.26 |
| | 50 seconds | 28.6 | 23.4 | 31 | 0.24 |
| | Difference | 1.0 | 0.1 | 4 | 0.02 |

(1): [×10$^{-7}$ · cm$^3$ · g · s$^{-1}$]

TABLE 12

| | Particulate water absorbing agent | Shaker-Mixer | Vibrating step | Truck transport (shaking) | Dropping time for latter sampling |
|---|---|---|---|---|---|
| Experimental Examples 1-2 to 6-2 | (a-1) | X | ○ | ○ | |
| Experimental Examples 7-2 | (a-1) | X | X | ○ | |
| Experimental Examples 8-2 | (a-2) | ○ | X | — | |
| Experimental Examples 9-2 | (a-2) | ○ | ○ | — | |
| Experimental Examples 10-2 | (a-2) | ○ | ○ | ○ | 80 seconds |
| Experimental Examples 11-2 | (a-2) | ○ | X | ○ | 80 seconds |
| Experimental Examples 12-2 | (b-2) | ○ | ○ | ○ | |
| Experimental Examples 13-2 | (b-2) | ○ | X | ○ | |
| Experimental Examples 14-2 | (c-2) | ○ | X | — | |
| Experimental Examples 15-2 | (c-2) | ○ | ○ | ○ | 75 seconds |
| Experimental Examples 16-2 | (c-2) | ○ | X | ○ | 75 seconds |

According to the invention, it is possible to significantly decrease the variations (relative deviations) of water absorption physical property values of the respective final products (absorbent articles), and also it is possible to provide a highly precise sampling method of the filled particulate water absorbing agent and thus it is possible to provide a technique in which a decrease in physical properties is suppressed or consumer complaints are diminished.

INDUSTRIAL APPLICABILITY

The filling method and sampling method in accordance with the present invention can be applied to the filling and sampling of a particulate water absorbing agent. This particulate water absorbing agent can be suitably applied to the manufacture of an absorbent article such as a sanitary

TABLE 12

| | CRC | | | AAP | | | FSR | | | SFC | | |
|---|---|---|---|---|---|---|---|---|---|---|---|---|
| | Average [g/g] | Standard deviation | Relative standard deviation | Average [g/g] | Standard deviation | Relative standard deviation | Average [g/g/s] | Standard deviation | Relative standard deviation | Average [(1)] | Standard deviation | Relative standard deviation |
| Experimental Example 1-2 | 27.4 | 0.15 | 0.6% | 24.0 | 0.08 | 0.3% | 0.36 | 0.017 | 4.8% | 97 | 5.3 | 5.4% |
| Experimental Example 2-2 | 27.0 | 0.23 | 0.9% | 24.0 | 0.11 | 0.4% | 0.38 | 0.012 | 3.1% | 94 | 2.3 | 2.4% |
| Experimental Example 3-2 | 27.2 | 0.23 | 0.8% | 24.0 | 0.08 | 0.3% | 0.37 | 0.012 | 3.2% | 97 | 2.6 | 2.7% |
| Experimental Example 4-2 | 27.2 | 0.32 | 1.2% | 24.2 | 0.14 | 0.6% | 0.36 | 0.014 | 3.9% | 98 | 3.8 | 3.9% |
| Experimental Example 5-2 | 27.0 | 0.16 | 0.6% | 23.8 | 0.09 | 0.4% | 0.39 | 0.014 | 3.4% | 94 | 2.8 | 3.0% |
| Experimental Example 6-2 | 27.0 | 0.32 | 1.2% | 23.9 | 0.09 | 0.4% | 0.38 | 0.014 | 3.7% | 101 | 3.9 | 3.9% |
| Total | 27.1 | 0.29 | 1.1% | 24.0 | 0.14 | 0.6% | 0.37 | 0.018 | 4.9% | 97 | 4.2 | 4.4% |
| Experimental Example 7-2 | 27.0 | 0.73 | 2.7% | 23.9 | 0.38 | 1.6% | 0.36 | 0.027 | 7.5% | 96 | 8.8 | 9.2% |

(1): [×10$^{-7}$ · cm$^3$ · g · s$^{-1}$]

material including an absorber, for example, paper diapers, sanitary napkins, and napkins for incontinents.

REFERENCE SIGNS LIST

2: Filling apparatus
4: Hopper
6: Intermediate portion
8: Discharge control unit
10: Mounting portion
12: Vibration generator (10 and 12 are together referred to as vibrating body)
14: Frame
16: Filling container (flexible container bag)
16: Discharge port
20: Hanging belt
22: Hanging portion
24: Upper surface of mounting portion
26: Pallet Incidentally, the entire contents of the prior Japanese Patent Application No. 2013-203059 filed on Sep. 30, 2013 and the prior Japanese Patent Application No. 2014-089598 filed on Apr. 23, 2014 are incorporated in this application by reference.

The invention claimed is:

1. A filled particulate water absorbing agent, wherein a relative standard deviation of respective water absorption physical property values of particulate water absorbing agents sampled from the same filled particulate water absorbing agent at three or more points satisfies at least one of the following (a) to (d):
   (a) a relative standard deviation of a centrifuge retention capacity (CRC) is 2% or less;
   (b) a relative standard deviation of a saline flow conductivity (SFC) is 6% or less;
   (c) a relative standard deviation of an absorbency against pressure (AAP) is 1% or less; and
   (d) a relative standard deviation of a free swell rate (FSR) is 5% or less, and
   wherein the filled particulate water absorbing agent is filled by a filling method comprising a filling step of filling a particulate water absorbing agent into a filling container; and
   a vibrating step of vibrating the filling container at the outside of the filling container, the vibrating step being conducted at least one time between the start and the end of the filling step, wherein
   a vibration condition in the vibrating step satisfies the following conditions (a) and (b);
   (a) vibration by a vibrating body in contact with the filling container has a vertical directional component and a vibrational angle is within 90°±30°; and
   (b) total amplitude at no load and a vibration frequency at no load of the vibrating body are set such that the following Equation 1-1 and Equation 2 or Equation 1-2 and Equation 2 are satisfied:

[Mathematical Formula 1]

$1 \leq$ acceleration $(G) \leq 13$ in a case in which final filling amount of particulate water absorbing agent per filling container: $W2 \geq 100$ kg (Equation 1-1)

$1 \leq$ acceleration $(G) \leq 15$ in a case in which final filling amount of particulate water absorbing agent per filling container: $W2 < 100$ kg (Equation 1-2)

[Mathematical Formula 2]

$27.0 \leq$ vibration index $\leq 44.0$ (Equation 2)

Incidentally, the acceleration and the vibration index are values calculated by the following Equation 3 and Equation 4, respectively;

[Mathematical Formula 3]

$$\text{Acceleration}[G] = \frac{\text{total amplitude at no load [mm]} \times (2\pi \times \text{vibration frequency at no load [Hz]})^2}{2 \times 1000 \times 9.8} \quad \text{(Equation 3)}$$

[Mathematical Formula 4]

$$\text{Vibration index} = 42 - 0.29 \times \text{vibration frequency at no load[Hz]} + 1.24 \times \text{acceleration}[G]. \quad \text{(Equation 4)}$$

2. The filled particulate water absorbing agent according to claim 1, wherein arithmetic mean values of the respective water absorption physical property values of particulate water absorbing agents sampled at three or more points satisfy at least one of the following (e) to (h):
   (e) CRC is from 5 (g/g) to 40 (g/g);
   (f) SFC is 20 ($\times 10^{-7} \cdot \text{cm}^3 \cdot \text{s} \cdot \text{g}^{-1}$) or more;
   (g) AAP is 20 (g/g) or more; and
   (h) FSR is 0.25 (g/g/s) or more.

3. The filled particulate water absorbing agent according to claim 1, wherein a bulk specific gravity of a particulate water absorbing agent is from 0.50 (g/ml) to 0.70 (g/ml).

4. The filled particulate water absorbing agent according to claim 1, wherein the filled particulate water absorbing agent is constituted by containing a water absorbent resin, the water absorbent resin being irregular crushed particles.

5. The filled particulate water absorbing agent according to claim 1, wherein sampling is conducted by a method of sampling a filled particulate water absorbing agent that is filled in a filling container and has a filling volume of V ($\text{cm}^3$), wherein
   when a sampling number n (times) of the same filled particulate water absorbing agent and a distance x (cm) among the respective sampling points adjacent to one another are set, the following conditions (1) and (2) are necessarily satisfied:

[Mathematical Formula 5]

$n \geq m$ (1)

with the proviso that, m is greater one of 3 and $\lfloor V/100000 \rfloor$ [Mathematical Formula 6]

[Mathematical Formula 7]

$x \geq y$ (2)

with the proviso that $$y = \frac{\sqrt[3]{V}}{\lfloor \sqrt[3]{m} \rfloor + 1}.$$ [Mathematical Formula 8]

6. A storage method or a transport method of the filled particulate water absorbing agent according to claim 1.

7. An absorbent article comprising a particulate water absorbing agent subdivided at from 1 g to 100 g from the filled particulate water absorbing agent according to claim 1.

8. A method for manufacturing an absorbent article, the method comprising a step of preparing the filled particulate water absorbing agent according to claim 1.

* * * * *